US009096677B2

(12) United States Patent
Emlen et al.

(10) Patent No.: US 9,096,677 B2
(45) Date of Patent: Aug. 4, 2015

(54) HUMANEERED ANTI-FACTOR B ANTIBODY

(71) Applicant: Alexion Cambridge Corporation, Cheshire, CT (US)

(72) Inventors: Woodruff Emlen, Greenwood Village, CO (US); V. Michael Holers, Denver, CO (US); Peter Flynn, San Francisco, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

(21) Appl. No.: 13/722,071

(22) Filed: Dec. 20, 2012

(65) Prior Publication Data

US 2013/0216529 A1    Aug. 22, 2013

Related U.S. Application Data

(60) Continuation of application No. 13/115,810, filed on May 25, 2011, now abandoned, which is a division of application No. 12/049,233, filed on Mar. 14, 2008, now Pat. No. 7,964,705.

(60) Provisional application No. 60/906,816, filed on Mar. 14, 2007.

(51) Int. Cl.
| A61K 39/00 | (2006.01) |
| A61K 39/395 | (2006.01) |
| C07K 16/00 | (2006.01) |
| C12P 21/08 | (2006.01) |
| C07K 16/40 | (2006.01) |
| C07K 16/18 | (2006.01) |
| C07K 16/46 | (2006.01) |

(52) U.S. Cl.
CPC ............. *C07K 16/40* (2013.01); *C07K 16/18* (2013.01); *C07K 16/461* (2013.01); *A61K 2039/505* (2013.01); *C07K 2317/55* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| 4,845,083 | A | 7/1989 | Fortin et al. |
| 4,883,784 | A | 11/1989 | Kaneko |
| 5,679,546 | A | 10/1997 | Ko et al. |
| 5,869,615 | A | 2/1999 | Hourcade et al. |
| 5,976,540 | A | 11/1999 | Rittershaus et al. |
| 6,165,463 | A | 12/2000 | Platz et al. |
| 6,248,365 | B1 | 6/2001 | Romisch et al. |
| 6,458,360 | B1 | 10/2002 | Fearon et al. |
| 6,521,450 | B1 | 2/2003 | Atkinson et al. |
| 6,820,011 | B2 | 11/2004 | Chen et al. |
| 6,897,290 | B1 | 5/2005 | Atkinson et al. |
| 7,759,304 | B2 | 7/2010 | Gilkeson et al. |
| 7,964,105 | B2 | 6/2011 | Moss |
| 7,964,705 | B2 | 6/2011 | Emlen et al. |
| 7,999,082 | B2 | 8/2011 | Holers et al. |
| 8,007,804 | B2 | 8/2011 | Tomlinson et al. |
| 2002/0015701 | A1 | 2/2002 | Gupta-Bansal et al. |
| 2002/0081293 | A1 | 6/2002 | Fung et al. |
| 2003/0198636 | A1 | 10/2003 | Gupta-Bansal et al. |
| 2003/0235582 | A1 | 12/2003 | Singh et al. |
| 2004/0014782 | A1 | 1/2004 | Krause |
| 2005/0107319 | A1 | 5/2005 | Bansal |
| 2005/0169915 | A1 | 8/2005 | Do Couto et al. |
| 2005/0255552 | A1 | 11/2005 | Flynn et al. |
| 2005/0260198 | A1 | 11/2005 | Holers et al. |
| 2006/0002944 | A1 | 1/2006 | Ashkenazi et al. |
| 2006/0134098 | A1 | 6/2006 | Bebbington et al. |
| 2006/0178308 | A1 | 8/2006 | Schwaeble et al. |
| 2006/0263819 | A1 | 11/2006 | Hageman et al. |
| 2006/0292141 | A1 | 12/2006 | Holers et al. |
| 2007/0020647 | A1 | 1/2007 | Hageman et al. |
| 2007/0065433 | A1 | 3/2007 | Mollnes et al. |
| 2007/0183970 | A1 | 8/2007 | Goldenberg et al. |
| 2008/0075720 | A1 | 3/2008 | Holers et al. |
| 2008/0102040 | A1 | 5/2008 | Holers et al. |
| 2008/0267980 | A1 | 10/2008 | Tomlinson et al. |

(Continued)

FOREIGN PATENT DOCUMENTS

| CA | 1340879 A | 1/2000 |
| WO | WO-99-42133 A1 | 8/1999 |

(Continued)

OTHER PUBLICATIONS

Mukherjee et al. 'Allergic Asthma: Influence of Genetic and Environmental Factors.' the Journal of Biological Chemistry vol. 286(38):32883-32889, 2011.*

Abe et al., "Contribution of anaphylatoxin C5a to late airway responses after repeated exposure of antigen to allergic rats," J Immunol. 167:4651-4660 (2001).

Abbas, et al., eds., *Cellular and Molecular Immunology*. W.B. Saunders Company, 54 (1991).

Abrahamsen et al., "Differential mediator release from basophils of allergic and non-allergic asthmatic patients after stimulation with anti-IgE and C5a," Clin Exp Allergy. 31:368-378 (2001).

(Continued)

*Primary Examiner* — Nora Rooney
(74) *Attorney, Agent, or Firm* — Clark & Elbing LLP; Kristina Bieker-Brady; Todd Armstrong

(57) ABSTRACT

This invention relates to humaneered anti-factor B antibodies and antigen-binding fragments thereof with reduced immunogenicity. The humaneered anti-factor B antibodies and antigen-binding fragments thereof are derived from murine monoclonal antibody 1379, which binds factor B in the third short consensus repeat ("SCR") domain and selectively inhibits activation of the alternative complement pathway by preventing formation of the C3bBb complex. The invention also relates to methods of treating diseases or disorders in which activation of the alternative complement pathway plays a role, and methods of selectively inhibiting activation of the alternative complement pathway in an individual in need thereof.

22 Claims, 6 Drawing Sheets

(56) References Cited

U.S. PATENT DOCUMENTS

| | | |
|---|---|---|
| 2008/0299114 A1 | 12/2008 | Emlen et al. |
| 2009/0175847 A1 | 7/2009 | Barghorn et al. |
| 2011/0163412 A1 | 7/2011 | Park |
| 2011/0318337 A1 | 12/2011 | Emlen et al. |
| 2012/0171206 A1 | 7/2012 | Tomlinson et al. |
| 2013/0029912 A1 | 1/2013 | Holers et al. |

FOREIGN PATENT DOCUMENTS

| | | |
|---|---|---|
| WO | WO-00/21559 A2 | 4/2000 |
| WO | WO-00-21559 A2 | 4/2000 |
| WO | WO-00-21559 A3 | 4/2000 |
| WO | WO-01-47963 A2 | 7/2001 |
| WO | WO-2004-022096 A1 | 3/2004 |
| WO | WO-2004-031240 A1 | 4/2004 |
| WO | WO-2004-103288 A2 | 12/2004 |
| WO | WO-2004-103288 A3 | 12/2004 |
| WO | WO-2004-106369 A2 | 12/2004 |
| WO | WO-2004-106369 A3 | 12/2004 |
| WO | WO-2005-003159 A1 | 1/2005 |
| WO | WO-2005-023195 A2 | 3/2005 |
| WO | WO-2005-023195 A3 | 3/2005 |
| WO | WO-2005-069970 A2 | 8/2005 |
| WO | WO-2005/077417 A1 | 8/2005 |
| WO | WO-2006-012621 A2 | 2/2006 |
| WO | WO-2006/055178 A2 | 5/2006 |
| WO | WO-2006-062716 A2 | 6/2006 |
| WO | WO-2006-062716 A3 | 6/2006 |
| WO | WO-2006-083533 A2 | 8/2006 |
| WO | WO-2006-083533 A3 | 8/2006 |
| WO | WO-2006/122257 A2 | 11/2006 |
| WO | WO-2007-011363 A2 | 1/2007 |
| WO | WO-2007-011363 A3 | 1/2007 |
| WO | WO-2007-029008 A2 | 3/2007 |
| WO | WO-2007-029008 A3 | 3/2007 |
| WO | WO-2007-032876 A2 | 3/2007 |
| WO | WO-2007-032876 A3 | 3/2007 |
| WO | WO-2007-056227 A2 | 5/2007 |
| WO | WO-2007-056227 A3 | 5/2007 |
| WO | WO-2008-140653 A2 | 11/2008 |
| WO | WO-2008-140653 A3 | 11/2008 |
| WO | WO-2008-140653 A9 | 11/2008 |
| WO | WO-2011/057158 A1 | 5/2011 |
| WO | WO-2011/143637 A1 | 11/2011 |
| WO | WO-2011/163412 A1 | 12/2011 |
| WO | WO-2013/177035 A2 | 11/2013 |

OTHER PUBLICATIONS

Alexander et al., "Complement-dependent apoptosis and inflammatory gene changes in murine lupus cerebritis," J Immunol. 175:8312-8319 (2005).

Anderson et al., "Activation of complement pathways after contusion-induced spinal cord injury," J Neurotrauma. 21:1831-1846 (2004).

Anonymous, "Monoclonal antibody to human factor B (Ba), Catalog No. A225," Quidel Corporation Product Catalog, <http://www.quidel.com/products/product_detail.php?prod=82&group=2>, retrieved on Aug. 4, 2008 (2 pages).

Anonymous, "Monoclonal antibody to human factor B (Bb), Catalog No. A227," Quidel Corporation Product Catalog, <http://www.quidel.com/products/product_detail.php?group=2&prod=83>, retrieved on Aug. 4, 2008 (2 pages).

Attwood, "The babel of bioinformatics," Science 290:471-473 (2000).

Barnum, "Inhibition of complement as a therapeutic approach in inflammatory central nervous system (CNS) disease," Mol Med. 5:569-582 (1999).

Becherer et al., "Segment spanning residues 727-768 of the complement C3 sequence contains a neoantigenic site and accommodates the binding of CR1, Factor H, and factor B," Biochemistry. 31:1787-1794 (1992).

Bellander et al., "Activation of the complement cascade and increase of clusterin in the brain following a cortical contusion in the adult rat," J Neurosurg. 85:468-475 (1996).

Bellander et al., "Complement activation in the human brain after traumatic head injury," J Neurotrauma. 18:1295-1311 (2001).

Bendayan, "Possibilities of false Immunocytochemical results generated by the use of monoclonal antibodies: The example of the anti-proinsulin antibody," J Histochem Cytochem. 43:881-886 (1995).

Bendig, "Humanization of rodent monoclonal antibodies by CDR grafting," Methods. 8:83-93, (1995).

Beste et al., "Small antibody-like proteins with prescribed ligand specificities derived from the lipocalin fold," Proc Natl Acad Sci USA. 96:1898-1903 (1999).

Bjornson et al., "Complement is activated in the upper respiratory tract during influenza virus infection," Am Rev Respir Dis. 143:1062-1066 (1991).

Blease et al., "Chemokines and their role in airway hyper-reactivity," Respir Res. 1:54-61 (2000).

Boos et al., "Murine complement C4 Is not required for experimental autoimmune encephalomyelitis," Glia. 49:158-160 (2004).

Bost et al., "Antibodies against a peptide sequence within the HIV envelope protein crossreacts with human interleukin-2," Immunol Invest. 17:577-586 (1988).

Brandis, "Acid-Base Physiology," <http://www.anaesthesiamcq.com/AcidBaseBook/ab4_4.php>, retrieved on Sep. 19, 2011 (2 pages).

Caldas et al., "Humanization of the anti-CD18 antibody 6.7: An unexpected effect of a framework residue in binding to antigen," Mol Immunol. 39:941-952 (2003).

Casale et al., "Direct evidence of a role for mast cells in the pathogenesis of antigen-induced bronchoconstriction," J Clin Invest. 80:1507-1511 (1987).

Casarsa et al., "Intracerebroventricular injection of the terminal complement complex causes inflammatory reaction in the rat brain," Eur J Immunol. 33:1260-1270 (2003).

Chaney, "Corticosteroids and cardiopulmonary bypass: A review of clinical investigations," Chest. 121:921-931 (2002).

Chàrdes et al., "Efficient amplification and direct sequencing of mouse variable regions from any immunoglobulin gene Family," FEBS Lett. 452:386-394 (1999).

Chen et al., "An experimental model of closed head injury in mice: pathophysiology, Histopathology, and cognitive deficits," J Neurotrauma. 13:557-568 (1996).

Chien et al., "Significant structural and functional change of an antigen-binding site by a distant amino acid substitution: proposal of a structural mechanism," Proc Natl Acad Sci USA. 86:5532-5536 (1989).

Choi et al., "Inhalation delivery of proteins from ethanol suspensions," Proc Natl Acad Sci. 98:11103-11107 (2001).

Cieslewicz et al., "The late, but not early, asthmatic response is dependent on IL-5 and correlates with eosinophil infiltration," J Clin Invest. 104:301-308 (1999).

Clardy et al., "Complement activation by whole endotoxin is blocked by a Monoclonal antibody to factor B," Infect Immun. 62:4549-4555 (1994).

Clardy et al., "In vitro inhibition of complement activation using a monoclonal antibody (McAb) directed against human Factor B (FB), Abstract No. 1969," Pediatric Res. 31:331 A (1992).

Clark, "Antibodies for therapeutic applications," <http://www.path.cam.ac.uk/~mrc7/humanisation/antibodies.html>, retrieved Jun. 1, 2002 (5 pages).

Clark, "Antibody humanisation for therapeutic applications," <http://www.path.cam.ac.uk/~mrc7/humanisation/index.html>, accessed Jun. 1, 2002 (4 pages).

Cole et al., "Beyond lysis: how complement influences cell fate," Clin Sci (Lond). 104:455-466 (2003).

Cole et al., "Complement regulator loss on apoptotic neuronal cells causes increased complement activation and promotes both phagocytosis and cell lysis," Mol Immunol. 43:1953-1964 (2006).

Collard et al., "Complement activation following oxidative stress," Mol Immunol. 36:941-948 (1999).

(56) References Cited

OTHER PUBLICATIONS

Crash trial collaborators, "Effect of intravenous corticosteroids on death within 14 days in 10008 adults with clinically significant head injury (MRC CRASH trial): Randomised placebo-controlled trial," Lancet. 364:1321-1328 (2004).
Czermak et al., "Complement, cytokines, and adhesion molecule expression in inflammatory reactions," Proc Assoc Am Physicians. 110(5):306-312 (1998).
Daha et al., "Stabilization of the amplification convertase of complement by monoclonal antibodies directed against human factor B," Infect Immun. 132:2538-2542 (1984).
De Broe et al., "Pathophysiology of hemodialysis-associated hypoxemia," Adv Nephrol Necker Hosp. 18:297-315, Abstract Only (1989).
Desai et al., "Demonstration of C5 cleaving activity in bronchoalveolar fluids and cells: A mechanism of acute and chronic alveolitis," J Exp Pathol. 1(3):201-216 (1984).
Diaz et al., "Leukocytes and mediators in bronchoalveolar lavage during allergen-induced late-phase asthmatic reactions," Am Rev Respir Dis. 139:1383-1389 (1989).
Drouin et al., "A protective role for the fifth complement component (C5) in allergic airway disease," Am J Respir Crit Care Med. 173:852-857 (2006).
Drouin et al., "Expression of the complement anaphylatoxin C3a and C5a receptors on bronchial epithelial and smooth muscle cells in models of sepsis and asthma," J Immunol. 166:2025-2032 (2001).
Dutton et al., "Traumatic Brain Injury," Curr Opin Crit Care. 9:503-509 (2003).
Eldadah et al., "Caspase pathways, neuronal apoptosis, and CNS injury," J Neurotrauma 17:811-829 (2000).
Elf et al., "Prevention of secondary insults in neurointensive care of traumatic brain injury," Eur J of Trauma. 29:74-80 (2003).
Elward et al., "CD46 plays a key role in tailoring innate immune recognition of apoptotic and necrotic cells," J Biol Chem. 280:36342-36354 (2005).
Farkas et al., "A neuronal C5a receptor and an associated apoptotic signal transduction pathway," J Physiol. 507:679-687 (1998).
Felderhoff-Mueser et al., "Pathways leading to apoptotic neurodegeneration following trauma to the developing rat brain," Neurobiol Dis. 11:231-245 (2002).
Figueroa et al., "Infectious diseases associated with complement deficiencies," Clin Microbiol Rev. 4:359-395 (1991).
Frank, "Complement: A brief review," J Allergy Clin Immunol. 84:411-420 (1989).
Friedlander, "Apoptosis and caspases in neurodegenerative diseases," N Engl J Med. 348:1365-1375 (2003).
Gerard et al., "Complement in allergy and asthma," Curr Opin Immunol. 14:705-708 (2002).
German et al., "Systemic complement depletion inhibits experimental cerebral vasospasm," Neurosurgery. 39:141-145, discussion 145-146, Abstract Only (1996).
Ghajar, "Traumatic brain injury," Lancet. 356:923-929 (2000).
Gilkeson, "Role of complement factor B in the pathogenesis of SLE, Project No. 5R01AI047469-05," <<http://projectreporter.nih.gov/pr_Prj_info_desc_dtls.cfm?icde=0&aid=6712799&print=yes>>, retrieved on Apr. 25, 2011 (2 pages).
Girardi et al., "Complement C5a receptors and neutrophils mediate fetal injury in the Antiphospholipid Syndrome," J. Clin. Invest. Corrigendum. 113:646 (2004).
Girardi et al., "Complement C5a receptors and neutrophils mediate fetal injury in the Antiphospholipid Syndrome," J. Clin. Invest. 112:1644-1653 (2003).
Giusti, et al. "Somatic diversification of S107 from an antiphosphocholine to an anti-DNA autoantibody is due to a single base change in its heavy chain variable region," Proc Natl Acad Sci USA. 84:2926-2930 (1987).
Glovsky, et al., "Complement determinations in human disease," Ann Allergy, Asthma Immunol. 93(6):513-523 (2004).
Glovsky et al., "Is complement activation a factor in bronchial asthma?" Int Arch Allergy Immunol. 118:330-332 (1999).
Gönczi et al., "The severity of clinical symptoms in ragweed-allergic patients is related to the extent of ragweed-induced complement activation in their sera," Allergy. 52:1110-1114 (1997).
Hall, "Cooperative Interaction of Factor B and other complement components with mononuclear cells in the antibody-independent lysis of xenogeneic erythrocytes," J Exp Med. 156:834-843 (1982).
Hawlisch et al., "The anaphylatoxins bridge innate and adaptive immune responses in allergic asthma," Mol Immunol. 41:123-131 (2004).
Hicks et al., "Vaccinia virus complement control protein enhances functional recovery after traumatic brain injury," J. Neurotrauma. 19:705-714 (2002).
Hogaboam et al., "Mannose-binding lectin deficiency alters the development of fungal asthma: Effects on airway response, inflammation, and cytokine profile," J Leukoc Biol. 75:805-814 (2004).
Holers et al., "The alternative pathway of complement in disease: Opportunities for therapeutic targeting," Mol. Immunol. 41:147-152 (2004).
Holers, "The complement system as a therapeutic target in autoimmunity," Clin Immunol. 107:140-151 (2003).
Holers, "Phenotypes of Complement Knockouts," Immunopharmacology. 49:125-131 (2000).
Holgate et al., "The bronchial epithelium as a key regulator of airway inflammation and remodelling in asthma," Clin Exp Allergy. 29:90-95 (1999).
Holm et al., "Functional mapping and single chain construction of the anti-cytokeratin 8 monoclonal antibody TS1," Mol. Immunol. 44:1075-1084 (2007).
Höpken et al., "The C5a chemoattractant receptor mediates mucosal defence to infection," Nature. 383:86-89 (1996).
Hourcade et al., "Analysis of the short consensus repeats of human complement factor B by site-directed mutagenesis," J Biol Chem. 270(34):19716-19722 (1995).
Hourcade et al., "Mutations of the type A domain of complement factor B that promote high-affinity C3b-binding," J Immunol. 162:2906-2911 (1999).
Humbles et al., "A role for the C3a anaphylatoxin receptor in the effector phase of asthma," Nature 406:998-1001 (2000).
Irvin et al., "Airways hyperreactivity and inflammation produced by aerosolization of human C5A des arg$^{1-3}$," Am Rev Respir Dis. 134:777-783 (1986).
Jaeschke et al., "Role of neutrophils in acute inflammatory livery injury," Liver Int. 26:912-919 (2006).
Jagels et al., "C3a and C5a enhance granulocyte adhesion to endothelial and epithelial cell monolayers: Epithelial and endothelial priming is required for C3a-induced eosinophil adhesion," Immunopharmacology. 46:209-222 (2000).
Kaczorowski et al., "Effect of Soluble Complement Receptor-1 on Neutrophil Accumulation After Traumatic Brain Injury in Rats," J Cereb Blood Flow Metab. 15:860-864 (1995).
Kang et al., "A novel anti-human Factor B monoclonal antibody inhibits Factor D-mediated associate and cleavage of Factor B," Abstract No. 191, Immunopharmacology. 49:68 (2000).
Karp et al., "Identification of complement factor 5 as a susceptibility locus for experimental allergic asthma," Nat Immunol. 1(3):221-226 (2000).
Kasamatsu et al., "Experimental acute lung injury in guinea pigs after aerosol challenge with sonicated *Pseudomonas aeruginosa* whole cells," Arerugi 42(10):1616-1622 (1993) English translation of abstract only.
Kodani et al., "Intratracheal administration of anaphylatoxin C5a potentiates antigen-induced pulmonary reactions through the prolonged production of cysteinyl-leukotrienes," Immunopharmacology. 49:263-274 (2000).
Köhl et al., "A regulatory role for the C5a anaphylatoxin in type 2 immunity in asthma," J Clin Invest. 116(3):783-796 (2006).
Kolb et al., "Ba and Bb fragments of factor B activation: Fragment production, biological activities, neoepitope expression and quantitation in clinical samples," Complement Inflamm. 6:175-204 (1989).
Kossmann et al., "Elevated levels of the complement components C3 and factor B in ventricular cerebrospinal fluid of patients with traumatic brain injury," J Neuroimmunol. 73:63-69 (1997).

(56) References Cited

OTHER PUBLICATIONS

Krug et al., "Complement factors C3a and C5a are increased in bronchoalveolar lavage fluid after segmental allergen provocation in subjects with asthma," Am J Respir Crit Care Med. 164:1841-1843 (2001).
Kulik et al., "Pathogenic natural antibodies recognizing Annexin IV are required to develop intestinal ischaemia-reperfusion injury and are selected during development in a CR2/CD21-dependent manner," Mol. Immunology. 45:4110, Abstract 045 (2008).
Kulkarni et al., "Neuroprotection from complement-mediated inflammatory damage," Ann N Y Acad Sci. 1035:147-164 (2004).
Kurucz et al., Current animal models of bronchial asthma, Curr Pharm Des. 12(25):3175-3194 (2006).
Kuttner-Kondo et al., "Characterization of the active sites in decay-accelerating factor," J Immunol. 167(4):2164-2171 (2001).
Kyrkanides et al., "Enhanced glial activation and expression of specific CNS inflammation-related molecules in aged versus young rats following cortical stab injury," J Neuroimmunol. 119:269-277 (2001).
Lambrecht, "An unexpected role for the anaphylatoxin C5a receptor in allergic sensitization," J Clin Invest. 116(3):628-632 (2006).
Langlois et al., "Complement activation occurs through both classical and alternative pathways prior to onset and resolution of adult Respiratory distress syndrome," Clin Immunol Immunopathol. 47:152-163 (1988).
Larsen et al., "A differential effect of C5a and C5a des Arg in the induction of pulmonary inflammation," Am J Pathol. 100:179-192 (1980).
Lederman et al., "A single amino acid substitution in a common African allele of the CD4 molecule ablates binding of the monoclonal antibody, OKT4," Mol Immunol. 28(11):1171-1181 (1991).
Leinhase et al., "Pharmacological complement inhibition at the C3 convertase level promotes neuronal survival, neuroprotective intracerebral gene expression, and neurological outcome after traumatic brain injury," Exp. Neurol. 199:454-464 (2006).
Leinhase et al., "Reduced neuronal cell death after experimental brain injury in mice lacking a functional alternative pathway of complement activation," BMC Neurosci. 7:55 (2006).
Lemanske, "Asthma therapies revisited: what have we learned?" Proc Am Thorac Soc. 6:312-315 (2009).
Leslie et al., "Complement Receptors," Encyclopedia of Life Sciences, Nature Publishing Group. (2001) (9 pages).
Li et al., "beta-Endorphin omission analogs: Dissociation of immunoreactivity from other biological activities." Proc Natl Acad Sci USA. 77(6):3211-3214 (1980).
Lukacs et al., "Complement-dependent immune complex-induced bronchial inflammation and hyperreactivity," Am J Physiol Lung Cell Mol Physiol. 280:L512-L518 (2001).
MacCallum et al., "Antibody-antigen interactions: Contact analysis and binding site topography." J Mol Biol. 262(5):732-45 (1996).
Marciano et al., "Neuron-specific mRNA complexity responses during hippocampal apoptosis after traumatic brain injury," J Neurosci. 24:2866-2876 (2004).
Mariuzza et al., The structural basis of antigen-antibody recognition, Annu Rev Biophys Chem. 16:139-159 (1987).
Marshall et al., "A new classification of head injury based on computerized tomography," J. Neurosurg. 75:S14-S20 (1991).
Maruo et al., "Generation of anaphylatoxins through proteolytic processing of C3 and C5 by house dust mite protease," J Allergy Clin Immunol. 100(2):253-260 (1997).
Matis et al., "Complement-specific antibodies: designing novel anti-inflammatories," Nat Med. 1(8):839-842 (1995).
Matsumoto et al., "Abrogation of the alternative complement pathway by targeted deletion of murine factor B," Proc Natl Acad Sci USA. 94(16):8720-8725 (1997).
Maulik et al., "Molecular biotechnology: therapeutic applications and strategies," Wiley-Liss, Inc., pp. v-viii (Table of Contents Only).
McArthur et al., "Moderate and severe traumatic brain injury: epidemiologic, imaging and neuropathologic perspectives," Brain Pathol. 14:185-194 (2004).
Mohamad et al., "Mitochondrial apoptotic pathways," Biocell. 29:149-161 (2005).
Morgan, "Regulation of the complement membrane attack pathway," Crit Rev Immunol. 19(3):173-198 (1999).
Mukherjee et al., "Allergic asthma: Influence of genetic and environmental factors," J Biol Chem. 286(38):32883-32889 (2011).
Nagata et al., "Activation of human serum complement with allergens," J Allergy Clin Immunol. 80(1):24-32 (1987).
Nagy et al., "The development of asthma in children infected with *Chlamydia pneumoniae* is dependent on the modifying effect of mannose-binding lectin," J Allergy Clin Immunol. 112:729-734 (2003).
Nataf et al., "Attenuation of experimental autoimmune demyelination in complement-deficient mice," J Immunol. 165(10):5867-5873 (2000).
Nataf et al., "Complement anaphylatoxin receptors on neurons: New tricks for old receptors?" Trends Neurosci. 22(9):397-402 (1999).
O'Barr et al., "Neuronal expression of a functional receptor for the C5a complement activation fragment," J Immunol. 166(6):4154-4162 (2001).
Ohlsson et al., "Complement activation after lumbosacral ventral root avulsion injury," Neurosci Lett. 394(3):179-183 (2006).
Ohlsson et al., "Complement activation following optic nerve crush in the adult rat," J. Neurotrauma. 20:895-904(2003).
Padlan et al., "Structure of an antibody-antigen complex: crystal structure of the HyHEL-10 Fab-lysozyme complex," Proc Natl Acad Sci USA. 86(15):5938-5942 (1989).
Peng et al., Late-breaking abstracts presented at scientific sessions AAAAI 62nd annual meeting, Mar. 3-7, "Blocking intrapulmonary activation of complement cascade on the development of airway hyperresponsiveness: Utility in sight?" Abstract LB2:720 (2006).
Peng et al., Abstract 200: "Contribution of complement component C5 in the development of airway inflammation, maintaining airway hyperresponsiveness and sustaining an ongoing asthmatic attack,"Abstracts/Mol Immunol. 41:292 (2004).
Peng et al., "Role of C5 in the development of airway inflammation, airway hyperresponsiveness, and ongoing airway response," J. Clin. Invest. 115(6):1590-1600(2005).
Peters et al., "The Bb fragment of complement factr B acts as a B cell growth factor." J Exp Med. 169(4):1225-1235 (1988).
Pillay et al., "Administration of vaccinia virus complement control protein shows significant cognitive improvement in a mild injury model," Ann. N. Y. Acad. Sci. 1056:450-461(2005).
Qiu et al., "Upregulation of the fas receptor death-inducing signaling complex after traumatic brain injury in mice and humans," J. Neurosci. 22(9):3504-3511(2002).
Rader et al., "A phage display approach for rapid antibody humanization: Designed combinatorial V gene libraries," Proc Natl Sci USA. 95:8910-8915 (1998).
Ramer et al., "Setting the stage for functional repair of spinal cord injuries: A cast of thousands," Spinal Cord. 43:134-161(2005).
Rancan et al., "Central nervous system-targeted complement inhibition mediates neuroprotection after closed head injury in transgenic mice," J. Cereb. Blood Flow. Metab. 23(9):1070-1074(2003).
Raghupathi et al., "BCL-2 overexpression attenuates cortical cell loss after traumatic brain injury in transgenic mice," J. Cereb. Blood Flow Metab. 18:1259-1269(1998).
Raghupathi, "Cell death mechanisms following traumatic brain injury," Brain Pathol. 14:215-222(2004).
Raghupathi et al., "Mild traumatic brain injury induces apoptotic cell death in the cortex that is preceded by decreases in cellular Bcl-2 immunoreactivity," Neuroscience. 110(4):605-616(2002).
Raghupathi et al., "Temporal alterations in cellular bax: Bcl-2 ratio following traumatic brain injury in the rat," J. Neurotrauma. 20(5):421-435(2003).
Rebhun et al., "Proteins of the complement system and acute phase reactants in sera of patients with spinal cord injury," Ann. Allergy 66:335-338(1991).
Reynolds et al., "Vaccinia Virus Complement Control Protein Reduces Inflammation and Improves Spinal Cord Integrity Following Spinal Cord Injury," Ann. NY. Acad. Sci. 1035:165-178(2004).

(56) References Cited

OTHER PUBLICATIONS

Rink et al., "Evidence of apoptotic cell death after experimental traumatic brain injury in the rat," Am. J. Pathol. 147:1575-1583(1995).
Robbins et al., "Complement activation by cigarette smoke," Am J. Physiol. 260: L254-L259 (1991).
Rood et al., "Reduction of early graft loss after intraportal porcine islet transplantation in monkeys," Transplantation. 83(2):202-210 (2007).
Roof et al., "Gender differences in acute CNS trauma and stroke: Neuroprotective effects of estrogen and progesterone," J. Neurotrauma 17(5):367-388(2000).
Rounioja et al., "Mechanism of acute fetal cardiovascular depression after maternal inflammatory challenge in mouse," Am J Pathol. 166(6):1585-1592 (2005).
Royo et al., "Pharmacology of traumatic brain injury," Current Opinion in Pharmacology 3:27-32(2003).
Rudikoff et al., "Single amino acid substitution altering antigen-binding specificity," Proc Natl Acad Sci USA. 79(6):1979-1983 (1982).
Sauerland et al., "A CRASH landing in severe head injury," Lancet. 364(9442):1291-1292 (2004).
Sambrook et al., Analysis of genomic DNA by Southern hybridization. *Molecular Cloning: A Laboratory Manual*. Second Edition, Cold Spring Harbor Labs Press: Cold Spring Harbor, NY, pp. 9.31-9.62(1989).
Schmidt et al., "Closed head injury—an inflammatory disease?," Brain Res. Rev. 48(2):388-399(2005).
Schmidt et al., "The role of neuroinflammation in traumatic brain injury," Eur. J. Trauma. 3:135-149(2004).
Schreiber et al., Abstract No. 042 "Complement anaphylatoxin C5a and C5a receptor are fundamental to neutrophil activation and glomerulonephritis induced by anti-neutrophil cytoplasmic antibodies," Abstracts/Mol Immunol. 45:4109(2008).
Sewell et al., "Complement C3 and C5 play critical roles in traumatic brain cryoinjury: Blocking effects on neutrophil extravasation by C5a receptor antagonist," J. Neuroimmunol. 155: 55-63(2004).
Shacka et al., "Regulation of neuronal cell death and neurodegeneration by members of the Bcl-2 family: Therapeutic implications," Curr Drug Targets CNS Neurol Disord. 4(1):25-39 (2005).
Sinha et al., Abstract No. 043 "The receptor for complement anaphylatoxin C5a protects against the development of airway hyperresponsiveness in allergic asthma by inhibiting cysteinyl leukotriene pathway," Abstracts/Mol Immunol. 45:4109-4110 (2008).
Singhrao et al., "Spontaneous classical pathway activation and deficiency of membrane regulators render human neurons susceptible to complement lysis," Am. J. Pathol. 157(3):905-918(2000).
Skolnick et al., "From genes to protein structure and function: novel applications of computational approaches in the genomic era," Trends Niotechnol. 18(1):34-39 (2000).
Stahel et al., "The role of the complement system in traumatic brain injury," Brain Res. Rev. 27(3):243-256(1998).
Stahel et al., "Experimental closed head injury: Analysis of neurological outcome, blood-brain barrier dysfunction, intracranial neutrophil infiltration, and neuronal cell death in mice deficient in genes for pro-inflammatory cytokines," J. Cereb. Blood Flow Metab. 20:369-380(2000).
Stahel et al., "Intracerebral complement C5a receptor (CD88) expression is regulated by TNF and lymphotoxin-α following closed head injury in mice," J. Neuroimmunol. 109:164-172(2000).
Stahel et al., "Intrathecal levels of complement-derived soluble membrane attack complex (sC5b-9) correlate with blood-brain barrier dysfunction in patients with traumatic brain injury," J. Neurotrauma. 18(8): 773-781(2001).
Strauss et al., "Common patterns of Bcl-2 family gene expression in two traumatic brain injury models," Neurotox. Res. 6(4):333-342(2004).
Stribling et al., "Aerosol gene delivery in vivo," Proc. Natl. Acad. Sci. USA. 89:11277-11281(1992).
Takafuji et al., "Degranulation from human eosinophils stimulated with C3a and C5a," Int Arch Allergy Immunol. 104(Suppl 1):27-29 (1994).
Takahashi et al., "Solubilization of antigen-antibody complexes: a new function of complement as a regulator of immune reactions," Prog Allergy. 27:134-166 (1980).
Tanaka et al., "Murine monoclonal anti-Ba antibody that enhances haemolytic activity of Factor B," Immunology. 73(4):383-387(1991).
Tatusova et al., "BLAST 2 Sequences, a new tool for comparing protein and nucleotide sequences," FEMS Microbiol Lett. 174(2):247-250 (1999).
Taube et al., "Factor B of the alternative complement pathway regulates development of airway hyperresponsiveness and inflammation," Proc Natl Acad Sci USA. 103(21):8084-8049 (2006).
Taube et al., "Inhibition of complement activation decreases airway inflammation and hyperresponsiveness," Am J Respir Cri. Care Med. 168:1333-1341 (2003).
Teasdale and Jennett, "Assessment of coma and impaired consciousness," Lancet. 2:81-84(1974).
Thurman et al., "Acute tubular necrosis is characterized by activation of the alternative pathway of complement," Kidney Int. 67:524-530 (2005).
Thurman et al., "The central role of the alternative complement pathway in human disease," J Immunol. 176(3):1305-1310 (2006).
Thurman et al., "Complement activation through the alternative pathway is necessary for the development of airway hyperresponsiveness (AHR) and inflammation in a model of human asthma," Mol Immunol., 41:319, Abstract No. 256.
Thurman et al., "Lack of a functional alternative complement pathway ameliorates ischemic acute renal failure in mice," J. Immunol. 170(3):1517-1523(2003).
Thurman et al., "A novel inhibitor of the alternative pathway of complement protects mice from ischemic acute renal failure," American Nephrology Society Meeting, Abstract (1 page).
Thurman et al., "A novel inhibitor of the alternative complement pathway prevents antiphospholipid antibody-induced pregnancy loss in mice," Mol Immunol. 42(1):87-97 (2005).
Thurman et al., "A novel inhibitor of the alternative complement pathway prevents antipospholid antibody-induced pregnancy loss in mice," Mol. Immunol. 41:318, Abstract No. 254 (2004).
Thurman et al., "Treatment with an inhibitory monoclonal antibody to mouse factor B protects mice from induction of apoptosis and renal ischemia/reperfusion injury," J Am Soc Nephrol. 17(3):707-715 (2006).
Ueda et al., "Probing Functional Sites on Complement Protein B with Monoclonal Antibodies," J. Immunol. 138(4):1143-1149(1987).
Van Beek et al., "Activation of the complement in the central nervous system: Roles in neurodegeneration and neuroprotection," Ann. N.Y. Acad. Sci. 992:56-71(2003).
Varsano et al., "Generation of complement C3 and expression of cell membrane complement inhibitory proteins by human bronchial epithelium cell line," Thorax. 55:364-369 (2000).
Versey et al., "Activation of complement in relation to disease," J Clin. Pathol., 28, Suppl. (Ass. Clin. Path.) 6:38-44(1975).
Vos et al., "EFNS guideline on mild traumatic brain injury: report of an EFNS task force," Eur. J. Neurol. 9:207-219(2002).
Wang et al., "Anti-C5 monoclonal antibody therapy prevents collagen-induced arthritis and ameliorates established disease," Proc Natl Acad Sci USA. 92:8955-8959 (1995).
Watanabe et al., "Modulation of renal disease in MRL/lpr mice genetically deficient in the alternative complement pathway factor B," J Immunol. 164(2):786-794 (2000).
Williams et al., "In situ DNA fragmentation occurs in white matter up to 12 months after head injury in man," Acta Neuropathol. 102:581-590 (2001).
Winkelstein et al., "The role of C3 as an opsonin in the early stages of infection," Proc Soc Exp Biol Med. 149:397-401 (1975).
Wong et al., "Apoptosis and traumatic brain injury," Neurocrit Care. 3:177-182 (2005).
Xiong et al., "Formation of complement membrane attack complex in mammalian cerebral cortex evokes seizures and neurodegeneration," J Neurosci. 23:955-960 (2003).

(56) References Cited

OTHER PUBLICATIONS

Xu et al., "Contribution of the complement control protein modules of C2 in C4b binding assessed by analysis of C2/factor B chimeras," J Immunol. 158(12):5958-5965 (1997).
Yakovlev et al., "Activation of CPP32-like caspases contributes to neuronal apoptosis and neurological dysfunction after traumatic brain injury," J Neurosci. 17:7415-7424 (1997).
Yao et al., "Progesterone differentially regulates pro- and anti-apoptotic gene expression in cerebral cortex following traumatic brain injury in rats," J Neurotrauma 22:656-668 (2005).
Yatsiv et al., "Elevated intracranial IL-18 in humans and mice after traumatic brain injury and evidence of neuroprotective effects of IL-18-binding protein after experimental closed head injury," J Cereb Blood Flow Metab. 22:971-978 (2002).
Yatsiv et al., "Erythropoietin is neuroprotective, improves functional recovery, and reduces neuronal apoptosis and inflammation in a rodent model of experimental closed head injury," FASEB J. 19:1701-1703 (2005).
Younger et al., "Detrimental effects of complement activation in hemorrhagic shock," J Appl Physiol. 90:441-446 (2001).
Younger et al., "Detrimental effects of complement activation in hemorrhagic shock," J Appl Physiol. 90:441-446, Corrigenda (2004). J Appl Physiol. 96:405.
Zhang et al., "Bench-to-bedside review: apoptosis/programmed cell death triggered by traumatic brain injury," Crit Care 9:66-75 (2005).
Zhang et al., "Bench-to-bedside review: Apoptosis/programmed cell death triggered by traumatic brain injury," Crit Care. 9(1):66-75 (2005).
Declaration of Joshua M. Thurman for U.S. Appl. No. 11/057,047, executed Apr. 16, 2008 (3 pages).
Declaration of Vernon Michael Holers for U.S. Appl. No. 11/057,047, executed Aug. 31, 2009 (68 pages).
European Patent Office Communication for European Application No. 08794326.2, dated Oct. 27, 2010 (7 pages).
Extended European Search Report for European Patent Application No. 10164673.5, dated Oct. 28, 2010 (10 pages).
Extended European Search Report for European Patent Application No. 10188613.3, dated May 31, 2011 (10 pages).
Final Office Action for U.S. Appl. No. 11/888,997 dated Aug. 22, 2011 (15 pages).
Final Office Action for U.S. Patent Application No. 11/1441,828, dated Jul. 21, 2011 (7 pages).
Final Office Action in U.S. Appl. No. 11/843,617, dated Jun. 21, 2011 (11 pages).
Final Office Action in U.S. Appl. No. 11/888,997, dated May 3, 2012 (10 pages).
International Preliminary Report on Patentability for PCT Application No. PCT/US2005/004346, mailed on Aug. 14, 2006 (4 pages).
International Preliminary Report on Patentability for PCT Patent Application No. PCT/US2006/020460, mailed Nov. 3, 2007 (6 pages).
International Preliminary Report on Patentability for PCT Patent Application No. PCT/US2008/003381, mailed on Sep. 15, 2009 (9 pages).
International Search Report for PCT Application No. PCT/US2008/003381, mailed Feb. 11, 2009 (6 pages).
International Search Report for PCT Application No. PCT/US2006/020460, mailed Aug. 29, 2006 (3 pages).
International Search Report for PCT Application No. PCT/US2005/04346, mailed Jul. 7, 2005 (2 pages).
Interview Summary for U.S. Appl. No. 11/057,047 mailed on Apr. 16, 2008 (4 pages).
Non-final Office Action in U.S. Appl. No. 11/057,047, dated Jan. 13, 2010 (13 pages).
Non-Final Office Action for U.S. Appl. No. 11/057,047, mailed on Oct. 19, 2007 (4 pages).
Non-Final Office Action for U.S. Appl. No. 11/057,047, mailed Apr. 30, 2009 (13 pages).
Non-Final Office Action for U.S. Appl. No. 12/049,233, mailed Aug. 16, 2010 (28 pages).
Non-Final Office Action for U.S. Appl. No. 11/843,617, mailed Oct. 7, 2010 (11 pages).
Non-Final Office Action for U.S. Appl. No. 11/057,047, mailed Oct. 13, 2010 (8 pages).
Non-Final Office Action for U.S. Appl. No. 11/888,997, mailed Nov. 29, 2010 (15 pages).
Non-Final Office Action for U.S. Appl. No. 11/441,828, mailed Jan. 28, 2011 (12 pages).
Non-Final Office Action mailed Dec. 19, 2011, for U.S. Appl. No. 11/888,997, filed Aug. 3, 2007 (9 pages).
Non-Final Office Action mailed Dec. 23, 2011, for U.S. Appl. No. 11/843,617, filed Aug. 22, 2007 (11 pages).
Notice of Allowance mailed Apr. 5, 2011, for U.S. Appl. No. 11/057,047, filed Feb. 10, 2005 (7 pages).
Notice of Allowance mailed Feb. 15, 2011, for U.S. Appl. No. 12/049,233, filed Mar. 14, 2008 (10 pages).
Reply to Final Office Action in U.S. Appl. No. 11/843,617, dated Aug. 22, 2011 (10 pages).
Reply to Final Office Action dated Jul. 3, 2012 in U.S. Appl. No. 11/888,997 (10 pages).
Reply to Final Office Action in U.S. Appl. No. 11/888,997, dated Nov. 5, 2012 (11 pages).
Reply to Final Office Action in U.S. Appl. No. 11/888,997, dated Nov. 22, 2011 (10 pages).
Reply to Final Office Action in U.S. Appl. No. 11/843,617, dated Oct. 10, 2011 (10 pages).
Reply to Final Office Action in U.S. Appl. No. 11/888,997, dated Oct. 24, 2011 (14 pages).
Reply to Non-Final Office Action in U.S. Appl. No. 11/843,617, dated Apr. 7, 2011 (12 pages).
Reply to Non-Final Office Action in U.S. Appl. No. 11/057,047, dated Apr. 16, 2008 (3 pages).
Reply to Non-Final Office Action in U.S. Appl. No. 11/057,047, dated Aug. 31, 2009 (22 pages).
Reply to Non-Final Office Action in U.S. Appl. No. 11/057,047, dated Jan. 13, 2011 (6 pages).
Reply to Non-final Office Action in U.S. Appl. No. 11/888,997, dated Mar. 19, 2012 (11 pages).
Reply to Non-Final Office Action in U.S. Appl. No. 11/843,617, dated Mar. 23, 2012 (10 pages).
Reply to Non-Final Office Action in U.S. Appl. No. 11/057,047, dated May 13, 2010 (18 pages).
Reply to Non-final Office Action in U.S. Appl. No. 11/888,997, dated May 26, 2011 (16 pages).
Supplementary Partial European Search Report, mailed on Jul. 7, 2008, for EP Application No. 05722948.6, filed Feb. 10, 2005 (7 pages).
Supplementary European Search Report mailed Nov. 24, 2011, for EP Application No. 06771303.2, filed May 26, 2006 (12 pages).
Written Opinion of the International Searching Authority mailed on Feb. 11, 2009, for International Application No. PCT/US2008/003381, filed on Mar. 14, 2008 (7 pages).
Written Opinion of the International Searching Authority mailed on Aug. 29, 2006, for International Application No. PCT/US2006/020460, filed on May 26, 2006 (4 pages).
Written Opinion of the International Searching Authority for International Application No. PCT/US05/04346, mailed on Jul. 7, 2005 (3 pages).
Morgan et al., "Expression of complement in the brain: Role in health and disease," Immunol Today. 17(10):461-466 (1996).
Chen et al., "An experimental model of closed head injury in mice: pathophysiology, histopathology, and cognitive deficits," J. Neurotrauma 13: 557-568, 1996.
Clardy, "Complement activation by whole endotoxin is blocked by a monoclonal antibody to factor B," Infect Immun. 62(10):4549-4555, 1994.
Gaetz, "The neurophysiology of brain injury," Clin Neurophysiology. 115:4-18 (2004).
Hourcade et al., "Analysis of the short consensus repeats of human complement factor B by site-directed mutagenesis," J. Biol. Chem. 270(34): 19716-19722, 1995.

(56) References Cited

OTHER PUBLICATIONS

Hourcade et al., "Mutations of the type A domain of complement factor B that promote high-affinity C3b-binding," J. Immunol. 162: 2906-2911, 1999.

International Search Report mailed on Aug. 29, 2006, for International Application No. PCT/US2006/020460, filed on May 26, 2006 (3 pages).

Keeling et al., "Local neutrophil influx following lateral fluid-percussion brain injury in rats is associated with accumulation of complement activation fragments of the third component (C3) of the complement system," J Neuroimmunol. 105:20-30 (2000).

Langlois et al., "Complement activation occurs through both classical and alternative pathways prior to onset and resolution of adult respiratory distress syndrome," Clin. Immunol. Immunopathol. 47: 152-163, 1988.

Thurman et al., "Lack of functional alternative complement pathway ameliorates ischemic acute renal failure in mice," J Immunol. 170: 1517-1523, 2003.

Ueda et al., "Probing functional sites on complement protein B with monoclonal antibodies," J. Immunol. 138: 1143-1149, 1987.

Versey et al., "Activation of complement in relation to disease," J. Clin. Pathol., 28, Suppl. (Assoc. Clin. Pathol) 6: 38-44, 1975.

Clark, "Antibody humanisation for therapeutic applications," <http://www.path.cam.ac.uk/~mrc7/humanisation/index.html> printed Jun. 1, 2002 (4 pages).

Sewell et al., "Complement C3 and C5 play critical roles in traumatic brain cryoinjury: blocking effects on neutrophil extravasation by C5a receptor antagonist," J. Neuroimmunol. 155: 55-63, 2004.

Singhrao et al., "Spontaneous classical pathway activation and deficiency of membrane regulators render human neurons susceptible to complement lysis," Am. J. Pathol. 157: 905-918, 2000.

Stahel et al., "The role of the complement system in traumatic brain injury," Brain Res. Rev. 27: 243-256, 1998.

International Search Report mailed on Feb. 11, 2009, for International Application No. PCT/US2008/003381, filed on Mar. 14, 2008 (3 pages).

International Search Report mailed on Jul. 7, 2005, for International Application No. PCT/US2005/004346, filed on Feb. 10, 2005 (2 pages).

"Monoclonal antibody to human factor B (Ba), Catalog No. A225," Quidel Corporation Product Catalog, <http://www.quidel.com/products/product_detail.php?group=2&prod=82>, retrieved on Aug. 4, 2008 (2 pages).

Kolb et al., "Ba and Bb fragments of Factor B activation: fragment production, biological activities, neoepitope expression and quantitation in clinical samples," Complement Inflamm. 6(3):175-204 (1989).

Xu, Y. et al., (1997) "Contribution of the complement control protein modules of C2 in C4b binding assessed by analysis of C2/factor B chimeras," J. Immunol. 158: 5958-5965.

Girardi et al., (Dec. 2003) "Complement C5a receptors and neutrophils mediate fetal injury in the Antiphospholipid Syndrome," J. Clin. Invest. 112(11):1644-1654.

Pardridge, "The blood-brain barrier and neurotherapeutics," NueroRx. 2(1):1-2 (2005).

May, "The Quest for an Acute Traumatic Brain Injury Treatment: Why Progesterone Could Be on Track to Become the First FDA-Approved Therapy," <www.news-medical.net>, retrieved on Feb. 10, 2014 (7 pages).

\* cited by examiner

Figure 2

| TA-V$_H$6 | 1 | EVQLQQSGPELVKPGASVKIPCKASGYTFT<u>DYNMD</u>WVKQSHGKSLEWIG<u>D</u> | SEQ ID NO:10 |
| TA-V$_H$7 | 1 | EVQLQQSGPELVKPGASVKIPCKASGYTFT<u>DYNMD</u>WVKQSHGKSLEWIG<u>D</u> | SEQ ID NO:11 |
| TA-V$_H$6 | 51 | <u>INPNNGGTIYNQKFKG</u>KATLTVDKSSSTAYMELRSLTSEDTAVYYCAR<u>GY</u> | SEQ ID NO:10 |
| TA-V$_H$7 | 51 | <u>INPNNGGTIYNQKFKG</u>KATLTVDKSSSTAYMELRSLTSEDTAVYYCAR<u>GY</u> | SEQ ID NO:11 |
| TA-V$_H$6 | 101 | <u>YSNSAWFAY</u>WGQGTLVTVSA   SEQ ID NO:10 | |
| TA-V$_H$7 | 101 | <u>YSNSAWFAY</u>WGQGTLVTVSA   SEQ ID NO:11 | |

| TA-V$_k$4 | 1 | DIVMSQSPSSLAVSAGEKVTMSC<u>KSSQSLLNSRTRKNYLA</u>WYQQKPGQSP | SEQ ID NO:9 |
| TA-V$_k$4 | 51 | KLLIY<u>WASTRES</u>GVPDRFTGSGSGTDFTLTISSVQAEDLAVYYC<u>KQSYNL</u> | |
| TA-V$_k$4 | 101 | <u>PWTF</u>GGGTKLEIKR | |

Figure 3

```
1379H      E V Q - - Q S G P E L V K P G A S V K I P    SEQ ID NO:31
TA-V_H6    E V Q L Q Q S G P E L V K P G A S V K I P    SEQ ID NO:33
```

```
1379L      D I V M S Q S P S S L A V S A G E K V T M S S K K    SEQ ID NO:32
TA-V_k4    D I V M S Q S P S S L A V S A G E K V T M S C K S    SEQ ID NO:34
```

Figure 4
ELISA: Reference TA003 Fab' binding to Factor B
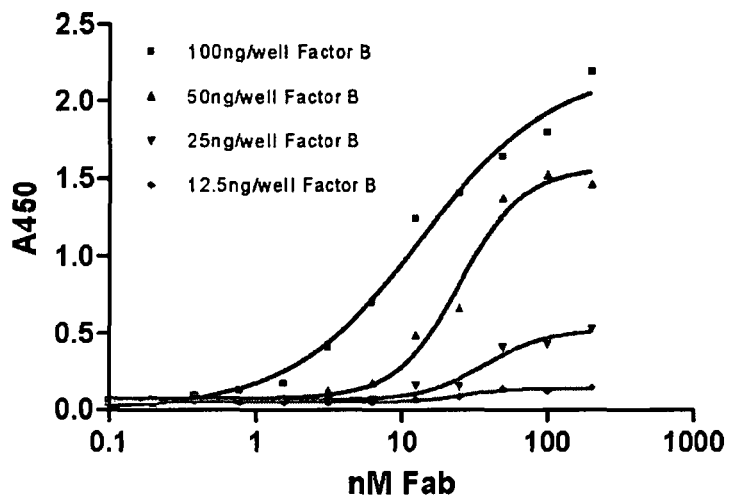
ELISA: Murine Fab (1379) binding to Factor B
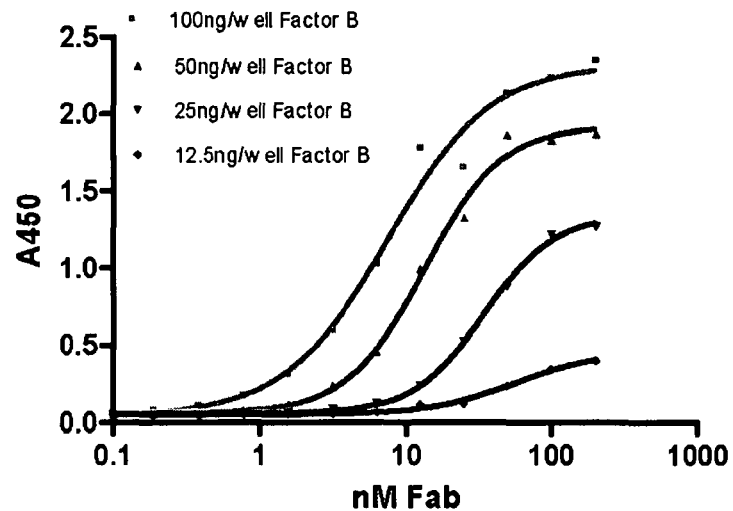

Figure 6

V_H Alignment

```
                              CDR1                                    CDR2
1-02/J_H4  1-QVQLVQSGAEVKKPGASVKVSCKASGYTF TGYYMH WVRQAPGQGLEWMG WINPNSGGTNYAQKFQGRVT    SEQ ID NO:13
TA10       1-EVQLQQSGPELVKPGASVKIPCKASGYTF TDYNMD WVKQSHGKSLEWIGD INPNNGTTYNQKFKGKAT     SEQ ID NO:15
TA101-1    1-QVQLVQSGAEVKKPGASVKVSCKASGYSF TDYYMT WVRQAPGQGLEWMG WINPNSGGTKYAQKFQGRVT   SEQ ID NO:17
TA102-4    1-QVQLVQSGAEVKKPGASVKVSCKASGYSF TDYYMI WVRQAPGQGLEWMG WINPNSGGTKYAQKFQGRVT   SEQ ID NO:19
TA103-2    1-QVQLVQSGAEVKKPGASVKVSCKASGYSF TDYYMH WVRQAPGQGLEWMG WINPNSGGTKYAQKFQGRVT   SEQ ID NO:21

CDR3
1-02/J_H4  70-MTRDTSISTAYMELSRLRSDDTAVYYCAR     YFDY WGQGTLVTVSS        SEQ ID NO:13
TA10       70-LTVDKSSSTAYMELRSLLSEDTAVYYCARGYYSNSAWFAY WGQGTLVTVSS      SEQ ID NO:15
TA101-1    70-MTRDTSISTAYMELSRLRSDDTAVYYCARGYYANSAWFAY WGQGTLVTVSS      SEQ ID NO:17
TA102-4    70-MTRDTSISTAYMELSRLRSDDTAVYYCARGYYANSAWFAY WGQGTLVTVSS      SEQ ID NO:19
TA103-2    70-MTRDTSISTAYMELSRLRSDDTAVYYCARGYYANSAWFAY WGQGTLVTVSS      SEQ ID NO:21
```

V_κ Alignment

```
                                                      CDR1                                        CDR2
V_κIV B3/J_κ2  1-DIVMTQSPDSLAVSLGERATINC KSSQSVLYSSNNKNYLA WYQQKPGQPPKLLIY WASTRES GVPD    SEQ ID NO:12
TA10           1-DIVMSQSPSSLAVSAGEKVTMSC KSSQSLLNSRTRKNYLA WYQQKPGQSPKLLIY WASTRES GVPD    SEQ ID NO:14
TA101-1        1-DIVMTQSPDSLAVSLGERATINC KSSQSLLNSSNKNYLA WYQQKPGQPPKLLIY WASTRES GVPD     SEQ ID NO:16
TA102-4        1-DIVMTQSPDSLAVSLGERATINC KSSQSVLNSRNKNYLA WYQQKPGQPPKLLIY WASTRES GVPD     SEQ ID NO:18
TA103-2        1-DIVMTQSPDSLAVSLGERATINC KSSQSLLNSRTKNYLA WYQQKPGQPPKLLIY WASTRES GVPD     SEQ ID NO:20

CDR3
VκIV B3/Jκ2  67-RFSGSGSGTDFTLTISSLQAEDVAVYYC QQYYSTPWT FGQGTKLEIK    SEQ ID NO:12
TA10         67-RFTGSGSGTDFTLTISSVQAEDIAVYYC QSYNLPWT FGQGTKLEIK     SEQ ID NO:14
TA101-1      67-RFSGSGSGTDFTLTISSLQAEDVAVYYCK QYNLPWT FGQGTKLEIK    SEQ ID NO:16
TA102-4      67-RFSGSGSGTDFTLTISSLQAEDVAVYYCK QVYNLPWT FGQGTKLEIK   SEQ ID NO:18
TA103-2      67-RFSGSGSGTDFTLTISSLQAEDVAVYYCK VYNLPWT FGQGTKLEIK    SEQ ID NO:20
``` ed States Patent (US 9,096,677 B2)

HUMANEERED ANTI-FACTOR B ANTIBODY

CROSS-REFERENCE TO RELATED APPLICATIONS

This application is a continuation of U.S. Application No. 13/115,810, filed on May 25, 2011, abandoned, which is a divisional of U.S. Application No. 12/049,233, filed on Mar. 14, 2008, now U.S. Pat. No. 7,964,705, which claims the benefit of U.S. Provisional Application No. 60/906,816, filed on Mar. 14, 2007, the disclosures of each of which are incorporated herein by reference in their entirety.

STATEMENT REGARDING FEDERALLY SPONSORED RESEARCH OR DEVELOPMENT

This invention was supported in part by Grant Nos. AI47469, HL-36577, HL-61005, and AI-31105, each awarded by the National Institutes of Health; and by Grant No. R825702 awarded by the Environmental Protection Agency. Thus, the government has certain rights to this invention.

REFERENCE TO A COMPACT DISC APPENDIX

Not applicable.

FIELD OF THE INVENTION

The present invention relates to novel engineered forms of a monoclonal antibody and antigen-binding fragments thereof that bind complement protein factor B and selectively inhibit the alternative complement pathway. The invention also generally relates to the use of such antibodies and antigen-binding fragments thereof to treat diseases in which the alternative complement pathway plays a role. In particular, the invention relates to the use of such antibodies and antigen-binding fragments thereof to inhibit activation of the alternative complement pathway, and to treat diseases in which activation of the alternative complement pathway is implicated. Such disorders include, but are not limited to, airway hyperresponsiveness and airway inflammation, ischemia-reperfusion injury, and related disorders in animals, including humans.

BACKGROUND OF THE INVENTION

Certain cells of the immune system produce proteins called antibodies or immunoglobulins ("Ig") in response to the presence of foreign proteins in the body, such as bacterial or viral proteins. Antibodies bind and neutralize foreign proteins in the body.

Antibodies generally bind their target protein antigens tightly and specifically, making them potentially useful therapeutics for treating a wide range of diseases characterized by altered protein expression. Many protein targets suitable for antibody-mediated disease therapy have been identified using non-human antibody molecules. For many therapeutic applications, however, the efficacy and safety of non-human antibodies is compromised because non-human Ig molecules are themselves immunogenic (i.e., capable of inducing an immune response). Thus, before antibodies can be approved for therapeutic use, they normally must be modified to reduce or eliminate their immunogenicity. Antibody Humaneering™ produces antibodies modified to reduce immunogenicity while retaining the ability to specifically bind their target antigen.

The present application describes the "humaneering" of a murine monoclonal antibody that binds factor B and selectively blocks the alternative complement pathway. The alternative complement pathway is usually activated by bacteria, parasites, viruses or fungi, although IgA antibodies and certain Ig light chains have also been reported to activate the pathway. Alternative pathway activation is initiated when circulating factor B binds to activated C3 (either C3b or C3H$_2$O). This complex is then cleaved by circulating factor D to yield an enzymatically active fragment, either C3bBb or C3(H$_2$O)Bb. These two enzymes can cleave circulating C3 generating C3b, which drives inflammation and also further amplifies the activation process, generating a positive feedback loop. Factor B is required to enable activation of the alternative pathway.

Recent studies have shown that the alternative pathway of complement plays an important role in the pathogenesis of several animal models of disease. Complement activation within the kidney after ischemia/reperfusion injury is mediated almost exclusively by the alternative pathway and the alternative pathway plays a critical role in the development of arthritis. Perhaps most surprisingly, mice deficient in the alternative pathway have been demonstrated to be protected from nephritis in the MRL/lpr model of lupus nephritis and from anti-phospholipid mediated fetal loss, disease models that would traditionally have been assumed to be mediated by the classical complement pathway.

The murine anti-factor B antibody from which the humaneered variants described herein were derived was produced by injecting factor B deficient mice ("fB$^{-/-}$") with a fusion protein comprising the second and third short consensus repeat ("SCR") domains of factor B fused to an immunoglobulin. The mice were then screened for antibodies to factor B. Spleen cells from an injected mouse producing anti-factor B antibodies were fused to myeloma cells according to standard procedures known in the art. One of the resulting hybridoma cells, number 1379, produced an IgG$_1$ antibody ("mAb 1379") that completely inhibits activation of the alternative complement pathway in vitro and in vivo. Antigen-binding Fab' fragments of mAb 1379 also completely inhibit activation of the alternative complement pathway. The hybridoma cell line that produces mAb 1379 has been deposited with the American Type Culture Collection ("ATCC") under Deposit No. PTA-6230.

Epitope mapping showed that mAb 1379 binds to factor B within the third SCR domain. Further experiments demonstrated that mAb 1379 inhibits alternative complement activation by preventing formation of the C3bBb complex. Finally, mAB 1379 binds an epitope conserved across multiple mammalian species, as shown by its ability to inhibit alternative complement activation in serum from a number of different species, including mice, rats, humans, baboons, rhesus monkeys, cynomolgous monkeys, pigs, rabbits, and horses. The production and characterization of anti-factor B antibody mAb 1379 is described in greater detail in U.S. Patent Publication No. US 2005/0260198 A1, which is incorporated herein by reference.

All references cited herein, including patent applications and publications, are hereby incorporated by reference in their entirety.

BRIEF SUMMARY OF THE INVENTION

In one aspect, the present invention provides a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex, wherein the humaneered antibody or antigen-binding fragment thereof has an equilibrium dissociation constant ("$K_D$") between about $1.0 \times 10^{-8}$ M and about $1.0 \times 10^{-10}$ M. In certain embodiments, the humaneered anti-factor B antibody or antigen-binding fragment thereof has a $K_D$ between about $1.0 \times 10^{-9}$ M and $9.0 \times 10^{-9}$ M, or between about $3.0 \times 10^{-9}$ M and $7.0 \times 10^{-9}$ M. In certain embodiments, the humaneered anti-factor B antibody or antigen-binding fragment thereof has a $K_D$ of about $3.7 \times 10^{-9}$ M or less, about $4.5 \times 10^{-9}$ M or less, about $5.4 \times 10^{-9}$ M or less, or about $6.5 \times 10^{-9}$ M or less.

In a related aspect, the present invention provides a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex, wherein the humaneered antibody or antigen-binding fragment thereof has a $K_D$ between about $1.0 \times 10^{-8}$ M and about $1.0 \times 10^{-10}$ M. In certain embodiments, the humaneered anti-factor B antibody or antigen-binding fragments thereof comprises a $V_\kappa$-region polypeptide selected from the group consisting of SEQ ID NO: 14 (TA10 reference antibody), SEQ ID NO: 16 (TA101-1 Fab'), SEQ ID NO: 18 (TA102-4 Fab'), and SEQ ID NO: 20 (TA103-2 Fab'), and a $V_H$-region polypeptide selected from the group consisting of SEQ ID NO: 15 (TA10 reference antibody), SEQ ID NO: 17 (TA101-1 Fab'), SEQ ID NO: 19 (TA102-4 Fab'), and SEQ ID NO: 21 (TA103-2 Fab'). In certain embodiments, the humaneered anti-factor B antibody or antigen-binding fragment thereof comprises a $V_\kappa$-region polypeptide comprising SEQ ID NO: 14 (TA10 reference antibody) and a $V_H$-region polypeptide comprising SEQ ID NO: 15 (TA10 reference antibody), and has a $K_D$ of $6.55 \times 10^{-9}$ M or less. In certain embodiments, the humaneered anti-factor B antibody or antigen-binding fragment thereof comprises a $V_\kappa$-region polypeptide comprising SEQ ID NO: 16 (TA101-1 Fab') and a $V_H$-region polypeptide comprising SEQ ID NO: 17 (TA101-1 Fab'), and has a $K_D$ of $4.53 \times 10^{-9}$ M or less. In certain embodiments, the humaneered anti-factor B antibody or antigen-binding fragment thereof comprises a $V_\kappa$-region polypeptide comprising SEQ ID NO: 18 (TA102-4 Fab') and a $V_H$-region polypeptide comprising SEQ ID NO: 19 (TA102-4 Fab'), and has a $K_D$ of $5.40 \times 10^{-9}$ M or less. In certain embodiments, the humaneered anti-factor B antibody or antigen-binding fragment thereof comprises a $V_\kappa$-region polypeptide comprising SEQ ID NO: 20 (TA103-2 Fab') and a $V_H$-region polypeptide comprising SEQ ID NO: 21 (TA103-2 Fab'), and has a $K_D$ of $3.73 \times 10^{-9}$ M or less. In certain embodiments, the humaneered anti-factor B antibody or antigen-binding fragment thereof comprises an antigen-binding fragment selected from the group consisting of Fab', (Fab')$_2$, Fv, scFv, and diabodies. In certain embodiments, the antigen-binding fragment of a humaneered anti-factor B antibody is a Fab'. In certain embodiments, the humaneered anti-factor B antibody or antigen-binding fragment thereof has a $K_D$ of about $3.7 \times 10^{-9}$ M or less, about $4.5 \times 10^{-9}$ M or less, about $5.4 \times 10^{-9}$ M or less, or about $6.5 \times 10^{-9}$ M or less.

In certain embodiments, the humaneered anti-factor B antibody or antigen-binding fragments thereof comprises a $V_\kappa$-region polypeptide selected from the group consisting of SEQ ID NO: 16 (TA101-1 Fab'), SEQ ID NO: 18 (TA102-4 Fab'), and SEQ ID NO: 20 (TA103-2 Fab'), and a $V_H$-region polypeptide selected from the group consisting of SEQ ID NO: (TA101-1 Fab'), SEQ ID NO: 36 (TA102-4 Fab'), and SEQ ID NO: 37 (TA103-2 Fab'). In certain embodiments, the humaneered anti-factor B antibody or antigen-binding fragment thereof comprises a $V_\kappa$-region polypeptide comprising SEQ ID NO: 16 (TA101-1 Fab') and a $V_H$-region polypeptide comprising SEQ ID NO: 35 (TA101-1 Fab'). In certain embodiments, the humaneered anti-factor B antibody or antigen-binding fragment thereof comprises a $V_\kappa$-region polypeptide comprising SEQ ID NO: 18 (TA102-4 Fab') and a $V_H$-region polypeptide comprising SEQ ID NO: 36 (TA102-4 Fab'). In certain embodiments, the humaneered anti-factor B antibody or antigen-binding fragment thereof comprises a $V_\kappa$-region polypeptide comprising SEQ ID NO: 20 (TA103-2 Fab') and a $V_H$-region polypeptide comprising SEQ ID NO: 37 (TA103-2 Fab').

In certain embodiments, the humaneered anti-factor B antibody or antigen-binding fragment thereof comprises a $V_\kappa$-region polypeptide selected from the group consisting of SEQ ID NO: 14 (TA10 reference antibody), SEQ ID NO: 16 (TA101-1 Fab'), SEQ ID NO: 18 (TA102-4 Fab'), and SEQ ID NO: 20 (TA103-2 Fab'), wherein the amino acid sequence of the $V_\kappa$-region polypeptide is about 80% identical to the closest human germline $V_\kappa$-region polypeptide, about 85% identical to the closest human germline $V_\kappa$-region polypeptide, about 90% identical to the closest human germline $V_\kappa$-region polypeptide, or about 95% identical to the closest human germline $V_\kappa$-region polypeptide. In certain embodiments, the humaneered anti-factor B antibody or antigen-binding fragment thereof comprises a $V_H$-region polypeptide selected from the group consisting of SEQ ID NO: 15 (TA10 reference antibody), SEQ ID NO: 17 (TA101-1 Fab'), SEQ ID NO: 19 (TA102-4 Fab'), and SEQ ID NO: 21 (TA103-2 Fab'), wherein the amino acid sequence of the $V_H$-region polypeptide is about 80% identical to the closest human germline $V_H$-region polypeptide, about 85% identical to the closest human germline $V_H$-region polypeptide, about 90% identical to the closest human germline $V_H$-region polypeptide, or about 95% identical to the closest human germline $V_H$-region polypeptide. In certain embodiments, the humaneered anti-factor B antibody or antigen-binding fragments thereof comprises a $V_\kappa$-region polypeptide selected from the group consisting of SEQ ID NO: 14 (TA10 reference antibody), SEQ ID NO: 16 (TA101-1 Fab'), SEQ ID NO: 18 (TA102-4 Fab'), and SEQ ID NO: 20 (TA103-2 Fab'), and a $V_H$-region polypeptide selected from the group consisting of SEQ ID NO: 15 (TA10 reference antibody), SEQ ID NO: 17 (TA101-1 Fab'), SEQ ID NO: 19 (TA102-4 Fab'), and SEQ ID NO: 21 (TA103-2 Fab'), wherein the amino acid sequence of the $V_\kappa$-region polypeptide and the amino acid sequence of the $V_H$-region polypeptide are about 80% identical to the closest human germline $V_\kappa$-region polypeptide and the closest human germline $V_H$-region polypeptide, about 85% identical to the closest human germline $V_\kappa$-region polypeptide and the closest human germline $V_H$-region polypeptide, about 90% identical to the closest human germline $V_\kappa$-region polypeptide and the closest human germline $V_H$-region polypeptide, or about 95% identical to the closest human germline $V_\kappa$-region polypeptide and the closest human germline $V_H$-region polypeptide.

In a related aspect, the present invention provides a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex, wherein the humaneered antibody or antigen-binding fragment thereof has a $K_D$ between about $1.0 \times 10^{-8}$ M and about $1.0 \times 10^{-10}$ M. In certain embodiments, the humaneered anti-factor B antibody or antigen-binding fragments thereof comprises a Vκ-region comprising a binding specificity determinant ("BSD") derived from the third complementarity determining region ("CDR3") and the fourth framework region ("FR4") selected from the group consisting of SEQ ID NO: 22 (TA10 reference antibody), SEQ ID NO: 24 (TA101-1 Fab'), SEQ ID NO: 26 (TA102-4 Fab'), and SEQ ID NO: 28 (TA103-2 Fab'), and the $V_H$-region of the humaneered anti-factor B antibody or antigen-binding fragment thereof comprises a BSD derived from the CDR3-FR4 region selected from the group consisting of SEQ ID NO: 23 (TA10 reference antibody), SEQ ID NO: 25 (TA101-1 Fab'), SEQ ID NO: 27 (TA102-4 Fab'), and SEQ ID NO: 29 (TA103-2 Fab'). In certain embodiments, the humaneered anti-factor B antibody or antigen-binding fragment thereof comprises a $V_\kappa$-region BSD polypeptide comprising SEQ ID NO: 22 (TA10 reference antibody) and a $V_H$-region BSD polypeptide comprising SEQ ID NO: 23 (TA10 reference antibody), and has a $K_D$ of $6.55 \times 10^{-9}$ M. In certain embodiments, the humaneered anti-factor B antibody or antigen-binding fragment thereof comprises a $V_\kappa$-region BSD polypeptide comprising SEQ ID NO: 24 (TA101-1 Fab') and a $V_H$-region BSD polypeptide comprising SEQ ID NO: 25 (TA101-1 Fab'), and has a $K_D$ of $4.53 \times 10^{-9}$ M. In certain embodiments, the humaneered anti-factor B antibody or antigen-binding fragment thereof comprises a $V_\kappa$-region BSD polypeptide comprising SEQ ID NO: 26 (TA102-4 Fab') and a $V_H$-region BSD polypeptide comprising SEQ ID NO: 27 (TA102-4 Fab'), and has a $K_D$ of $5.40 \times 10^{-9}$ M. In certain embodiments, the humaneered anti-factor B antibody or antigen-binding fragment thereof comprises a $V_\kappa$-region BSD polypeptide comprising SEQ ID NO: 28 (TA103-2 Fab') and a $V_H$-region BSD polypeptide comprising SEQ ID NO: 29 (TA103-2 Fab'), and has a $K_D$ of $3.73 \times 10^{-9}$ M. In certain embodiments, the humaneered anti-factor B antibody or antigen-binding fragment thereof comprises an antigen-binding fragment selected from the group consisting of Fab', (Fab')$_2$, Fv, scFv, and diabodies. In certain embodiments, the antigen-binding fragment of a humaneered anti-factor B antibody is a Fab'.

In another aspect, the present invention provides a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex comprising a $V_\kappa$-region polypeptide selected from the group consisting of SEQ ID NO: 14 (TA10 reference antibody), SEQ ID NO: 16 (TA101-1 Fab'), SEQ ID NO: 18 (TA102-4 Fab'), and SEQ ID NO: 20 (TA103-2 Fab'), and a $V_H$-region polypeptide selected from the group consisting of SEQ ID NO: 15 (TA10 reference antibody), SEQ ID NO: 17 (TA101-1 Fab'), SEQ ID NO: 19 (TA102-4 Fab'), and SEQ ID NO: 21 (TA103-2 Fab'). In certain embodiments, the humaneered anti-factor B antibody or antigen-binding fragment thereof comprises a $V_\kappa$-region polypeptide comprising SEQ ID NO: 14 (TA10 reference antibody) and a $V_H$-region polypeptide comprising SEQ ID NO: 15 (TA10 reference antibody). In certain embodiments, the humaneered anti-factor B antibody or antigen-binding fragment thereof comprises a $V_\kappa$-region polypeptide comprising SEQ ID NO: 16 (TA101-1 Fab') and a $V_H$-region polypeptide comprising SEQ ID NO: 17 (TA101-1 Fab'). In certain embodiments, the humaneered anti-factor B antibody or antigen-binding fragment thereof comprises a $V_\kappa$-region polypeptide comprising SEQ ID NO: 18 (TA102-4 Fab') and a $V_H$-region polypeptide comprising SEQ ID NO: 19 (TA102-4 Fab'). In certain embodiments, the humaneered anti-factor B antibody or antigen-binding fragment thereof comprises a $V_\kappa$-region polypeptide comprising SEQ ID NO: 20 (TA103-2 Fab') and a $V_H$-region polypeptide comprising SEQ ID NO: 21 (TA103-2 Fab'). In certain embodiments, the humaneered anti-factor B antibody or antigen-binding fragment thereof comprises a $V_\kappa$-region polypeptide selected from the group consisting of SEQ ID NO: 14 (TA10 reference antibody), SEQ ID NO: 16 (TA101-1 Fab'), SEQ ID NO: 18 (TA102-4 Fab'), and SEQ ID NO: 20 (TA103-2 Fab'). In certain embodiments, the humaneered anti-factor B antibody or antigen binding fragment thereof comprises a $V_H$-region polypeptide selected from the group consisting of SEQ ID NO: 15 (TA10 reference antibody), SEQ ID NO: 17 (TA101-1 Fab'), SEQ ID NO: 19 (TA102-4 Fab'), and SEQ ID NO: 21 (TA103-2 Fab'). In certain embodiments, the humaneered anti-factor B antibody or antigen-binding fragment thereof comprises an antigen-binding fragment selected from the group consisting of Fab', (Fab')$_2$, Fv, scFv, and diabodies. In certain embodiments, the antigen-binding fragment of a humaneered anti-factor B antibody is a Fab'.

In another aspect, the present invention provides a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex, wherein the $V_\kappa$-region of the humaneered anti-factor B antibody or antigen-binding fragment thereof comprises a binding specificity determinant ("BSD") derived from the third complementarity determining region ("CDR3") and the fourth framework region ("FR4") selected from the group consisting of SEQ ID NO: 22 (TA10 reference antibody), SEQ ID NO: 24 (TA101-1 Fab'), SEQ ID NO: 26 (TA102-4 Fab'), and SEQ ID NO: 28 (TA103-2 Fab'), and the $V_H$-region of the humaneered anti-factor B antibody or antigen-binding fragment thereof comprises a BSD derived from the CDR3-FR4 region selected from the group consisting of SEQ ID NO: 23 (TA10 reference antibody), SEQ ID NO: 25 (TA101-1 Fab'), SEQ ID NO: 27 (TA102-4 Fab'), and SEQ ID NO: 29 (TA103-2 Fab'). In certain embodiments, the humaneered anti-factor B antibody or antigen-binding fragment thereof comprises a $V_\kappa$-region BSD polypeptide comprising SEQ ID NO: 22 (TA10 reference antibody) and a $V_H$-region BSD polypeptide comprising SEQ ID NO: 23 (TA10 reference antibody). In certain embodiments, the humaneered anti-factor B antibody or antigen-binding fragment thereof comprises a $V_\kappa$-region BSD polypeptide comprising SEQ ID NO: 24 (TA101-1 Fab') and a $V_H$-region BSD polypeptide comprising SEQ ID NO: 25 (TA101-1 Fab'). In certain embodiments, the humaneered anti-factor B antibody or antigen-binding fragment thereof comprises a $V_\kappa$-region BSD polypeptide comprising SEQ ID NO: 26 (TA102-4 Fab') and a $V_H$-region BSD polypeptide comprising SEQ ID NO: 27 (TA102-4 Fab'). In certain embodiments, the humaneered anti-factor B antibody or antigen-binding fragment thereof comprises a $V_\kappa$-region BSD polypeptide comprising SEQ ID NO: 28 (TA103-2 Fab') and a $V_H$-region BSD polypeptide comprising SEQ ID NO: 29 (TA103-2 Fab'). In certain embodiments, the $V_\kappa$-region of the humaneered anti-factor B antibody or antigen-binding fragment thereof comprises a binding specificity determinant ("BSD") derived from the third complementarity determining region ("CDR3") and the fourth framework region ("FR4") selected from the group consisting of SEQ ID NO: 22 (TA10 reference antibody), SEQ ID NO: 24 (TA101-1 Fab'), SEQ ID NO: 26 (TA102-4 Fab'), and SEQ ID NO: 28 (TA103-2 Fab'). In certain embodiments, the $V_H$-region of the humaneered anti-factor B antibody or antigen-binding fragment thereof comprises a BSD derived from the CDR3-FR4 region selected from the group consisting of SEQ ID NO: 23 (TA10 reference antibody), SEQ ID NO: 25 (TA101-1 Fab'), SEQ ID NO: 27 (TA102-4 Fab'), and SEQ ID NO: 29

(TA103-2 Fab'). In certain embodiments, the humaneered anti-factor B antibody or antigen-binding fragment thereof comprises an antigen-binding fragment selected from the group consisting of Fab', (Fab')$_2$, Fv, scFv, and diabodies. In certain embodiments, the antigen-binding fragment of a humaneered anti-factor B antibody is a Fab'.

In another aspect, the present invention provides methods of treating a disease or disorder in which activation of the alternative complement pathway plays a role, comprising administering a humaneered anti-factor B antibody or antigen-binding fragment thereof derived from murine monoclonal antibody 1379 ("mAb 1379") that selectively binds to factor B within the third short consensus repeat ("SCR") domain and prevents formation of the C3bBb complex, wherein the humaneered antibody or antigen-binding fragment thereof has an equilibrium dissociation constant ("KD") between about $1.0 \times 10^{-8}$ M and about $1.0 \times 10^{-10}$ M, to an individual that has, or is at risk of developing such a disease or disorder. In certain embodiments, the disease or disorder is airway hyperresponsiveness ("AHR") or airway inflammation. In certain embodiments, any of the humaneered anti-factor B antibodies or antigen-binding fragments thereof are administered to the individual in an amount effective to measurably reduce AHR in the animal as compared to before administration of the antibody or antigen-binding fragment thereof. In certain embodiments, AHR or airway inflammation is associated with a disease selected from the group consisting of asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hypereosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection. In certain embodiments, the AHR or airway inflammation is associated with allergic inflammation, asthma, or COPD.

In another aspect, the present invention provides methods of inhibiting activation of the alternative complement pathway in an individual that has, or is at risk of developing a condition or disease in which activation of the alternative complement pathway contributes to the condition or disease, exacerbates at least one symptom of the condition or disease, or causes the condition or disease, comprising administering any of the humaneered anti-factor B antibodies or antigen-binding fragments thereof disclosed herein to an individual in need thereof.

In another aspect, the present invention provides a composition comprising an effective amount of the humaneered anti-factor B antibody or antigen-binding fragments thereof disclosed herein and a pharmaceutically acceptable carrier. In certain embodiments, the pharmaceutically acceptable carrier is selected from the group consisting of: a dry, dispersible powder; anhydrous ethanol; small capsules; liposomes; a nebulized spray; and an injectable excipient.

BRIEF DESCRIPTION OF THE DRAWINGS

FIG. 2 is a comparison of amino acid sequences derived from $V_H$ and $V_\kappa$ cDNA sequences cloned from the hybridoma cell line producing mAb 1379.

FIG. 3 is a comparison of amino-terminal amino acid sequences derived from the cloned $V_A$ and $V_\kappa$ cDNA sequences to amino-terminal amino acid sequences determined from mAb 1379.

FIG. 4 is a comparison of factor B binding between the cloned Fab' TA003 and a Fab' derived from mAb 1379 by papain digestion.

FIG. 6 is a comparison of amino acid sequences derived from the sequence of humaneered antibody isolates TA101-1, TA102-4, and TA103-2 to the corresponding sequences from the reference antibody TA10 and from the closest human germline light and heavy chain variable domain genes ("$V_L$-" and "$V_H$-gene") and joining segments ("J-segment") (human $V_H 1$-$02/J_H 4$ and $V_\kappa IV$-B3/$J_\kappa 2$).

DETAILED DESCRIPTION OF THE INVENTION

Figure 1:
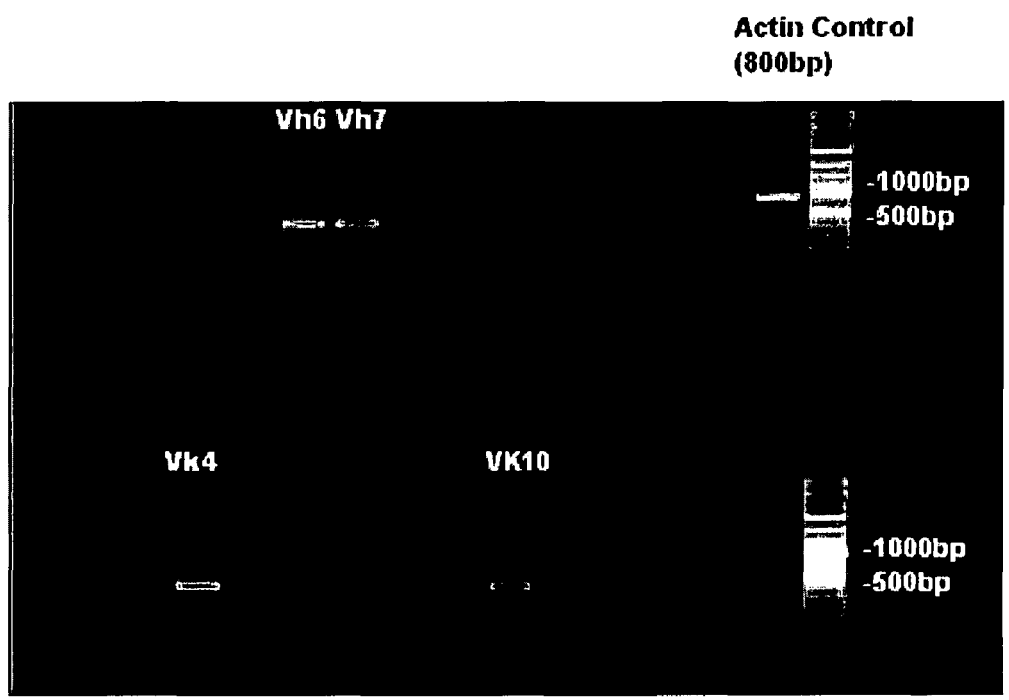
FIG. 1 is an agarose gel showing double-stranded cDNA products generated with degenerate V-region-specific primer sets using a template of first strand cDNA prepared from mRNA isolated from the hybridoma producing mAb 1379.

Humaneered anti-factor B antibodies or antigen-binding fragments thereof that selectively bind to complement factor B and selectively inhibit activation of the alternative complement pathway may be used to treat any disease or disorder involving the alternative complement pathway in animals, including humans. In particular, such antibodies or antigen-binding fragments thereof may be used to treat any disease or disorder in animals, including humans, in which activation of the alternative complement pathway plays a role. Such diseases or disorders include, for example, allergic asthma and the accompanying airway inflammation and airway hyperresponsiveness ("AHR"), chronic obstructive pulmonary disease ("COPD"), allergic bronchopulmonary aspergillosis, hypersensitivity pneumonia, eosinophilic pneumonia, emphysema, bronchitis, allergic bronchitis, bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection and adenovirus infection, and ischemia-reperfusion injury. See, e.g., U.S. Patent Publication No. US 2005/0260198 A1, which is incorporated herein by reference.

Allergic asthma is a common syndrome associated with airway inflammation and AHR. In patients with allergic asthma, exposure to inhaled allergen leads to an increase in AHR and airway inflammation. Studies have shown increased levels of biologically active fragments derived from the complement C3, C4 and C5 family of proteins, especially C3a and C5a in bronchioalveolar lavage ("BAL") fluid. This suggests that in these patients, activation of the complement pathway through an allergen-induced mechanism occurs in the lung after allergen exposure. Animal models have provided further insight in the role of complement for the development of allergic airway disease. Animals deficient in C3 or C3a receptor appear protected from the development of allergen induced airway disease. See, e.g., U.S. Patent Publication No. US 2005/0260198 A1, which is incorporated herein by reference.

DEFINITIONS

As used herein, the term "antibody" or "immunoglobulin" refers to glycoproteins of the immunoglobulin ("Ig") superfamily of proteins. An antibody or immunoglobulin ("Ig") molecule is tetrameric, comprising two identical light chain polypeptides and two identical heavy chain polypeptides (the terms "light chain polypeptide" and "light chain" or "heavy chain polypeptide" and "heavy chain" are used interchangeably herein to describe the polypeptides of an Ig molecule). The two heavy chains are linked together by disulfide bonds, and each heavy chain is linked to a light chain by a disulfide bond. Each full-length Ig molecule contains at least two binding sites for a specific target or antigen.

The immune system produces several different classes of 1 g molecules ("isotypes"), including IgA, IgD, IgE, IgG, and IgM, each distinguished by the particular class of heavy chain polypeptide present: alpha ("α") found in IgA, delta ("δ") found in IgD, epsilon ("ε") found in IgE, gamma ("γ") found in IgG, and mu ("μ") found in IgM. There are at least five different γ heavy chain polypeptides ("isotypes") found in IgG. In contrast, there are only light chain polypeptide isotypes, referred to as kappa ("κ") and lambda ("λ") chains. The distinctive characteristics of antibody isotypes are defined by sequences of the constant domains of the heavy chain.

An IgG molecule comprises two light chains (either κ or λ form) and two heavy chains (γ form) bound together by disulfide bonds. The κ and λ forms of IgG light chain both contain a domain of relatively variable amino acid sequences, called the variable region (variously referred to as a "$V_L$-," "$V_\kappa$-," or "$V_\lambda$-region") and a domain of relatively conserved amino acid sequences, called the constant region ("$C_L$-region"). Similarly, each IgG heavy chain contains a variable region ("$V_H$-region") and one or more conserved regions: a complete IgG heavy chain contains three constant domains ("$C_H1$-," "$C_H2$-," and "$C_H3$-regions") and a hinge region. Within each $V_L$- or $V_H$-region, hypervariable regions, also known as complementarity-determining regions ("CDR"), are interspersed between relatively conserved framework regions ("FR"). Generally, the variable region of a light or heavy chain polypeptide contains four FR and three CDR arranged in the following order along the polypeptide: $NH_2$-FR1-CDR1-FR2-CDR2-FR3-CDR3-FR4-COOH. Together the CDR and FR determine the three-dimensional structure of the IgG binding site and thus, the specific target protein or antigen to which that IgG molecule binds. Each IgG molecule is dimeric, able to bind two antigen molecules. Cleavage of a dimeric IgG with the protease papain produces two identical antigen-binding fragments ("Fab'") and an "Fc" fragment, so named because is readily crystallized.

As used herein, the term "antigen-binding fragment" refers to a fragment of an antibody or immunoglobulin molecule that retains the ability to specifically bind its cognate antigen. Antigen-binding fragments generally lack part or all of one or more functional domains present in full-length antibody or Ig molecules, such as those that confer the ability to fix complement and stimulate antibody-dependent cell-mediated cytoxicity ("ADCC"). Antigen-binding fragments can be prepared from full-length antibody isolates, for example, by digestion with proteases such as papain (which produces two identical monovalent antigen-binding fragments ("Fab'") comprising the variable and constant regions of an antibody light chain and the variable and first constant region of an antibody heavy chain) or pepsin (which produces a single bivalent antigen-binding fragment ("Fab')$_2$" comprising a pair of Fab' fragments covalently linked near their carboxyl termini).

Other antigen-binding fragments may be produced using standard recombinant DNA methodology, such as "Fv"fragments, single chain Fv antibodies ("scFv"), bi-specific antibodies, diabodies, humanized or humaneered antibodies, and the like. An "Fv" fragment is an antibody fragment that contains a complete antigen recognition and binding site, comprising a dimer of one $V_H$-region and one $V_L$-region. An "scFv" antibody fragment comprises the $V_H$-region and one $V_L$-region of an antibody in a single polypeptide chain. A "diabody" is a small antibody fragment with two antigen-binding sites, comprising a heavy chain variable domain connected to a light chain variable domain in the same polypeptide. By using a linker too short to allow the $V_H$- and $V_L$-regions of the same polypeptide to pair, the domains are forced to pair with complementary domains of a second polypeptide, creating two antigen-binding sites.

As used herein, the term "binding specificity determinant" or "BSD" refers to all or a portion of the amino acid sequence of the third complementarity determining region ("CDR3") and the fourth framework region ("FR4") of an IgG $V_L$ or $V_H$ polypeptide that mediates antigen-binding specificity of a particular Ig molecule. BSDs function in heavy chain and light chain pairs, such that a particular BSD comprises the amino acid sequence of CDR3-FR4 from a $V_L$-region paired with the amino acid sequence of CDR3-FR4 from a cognate $V_H$-region.

As used herein, the term "epitope" refers to a site on a larger molecule, such as a given protein, polypeptide, or antigen (i.e., factor B), to which an antibody, immunoglobulin, or antigen-binding fragment thereof will bind, and against which an antibody will be produced. The term "epitope" can be used interchangeably with the terms "antigenic determinant," "antibody binding site," or "conserved binding surface" of a given protein, polypeptide, or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential or linear epitope, or, in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions.

The epitope recognized by the mAb 1379, and shared by the humaneered variants described herein, is a conformational epitope that is not a linear epitope located within the three-dimensional structure of a portion of the third SCR domain of factor B. See, e.g., US 2005/0260198 A1, which is incorporated herein by reference in its entirety. Human factor B is expressed as a 764 amino acid preproprotein containing a twenty-five (25) amino acid signal peptide spanning amino acids 1-25 of its amino terminus. The amino acid sequence for human factor B preprotein is found in NCBI Database Accession No. P00751. Mature human factor B comprises the amino acid sequence of Accession No. P00751 lacking the twenty-five (25) amino acid signal peptide (i.e., SEQ ID NO: 30). The third SCR domain of mature human factor B extends from about position 137 to about position 195 of SEQ ID NO: 30. The portion that contains the epitope is the three-dimensional structure of factor B that is defined by substantially all of (e.g., at least about 90% of) amino acid positions Ala137-Ser192 of SEQ ID NO: 30, or equivalent positions in a non-human factor B sequence, when such sequence is conformationally arranged as it occurs in the natural full-length factor B sequence.

The murine mAb 1379 and the humaneered variants described herein bind to an epitope or conserved binding surface within or containing a part of the third SCR domain comprising an epitope of human factor B that includes at least a portion of the sequence comprising from about position Tyr139 to about position Ser185 of the mature human factor B protein (SEQ ID NO: 30), to an epitope of human factor B that includes at least a portion of the sequence comprising from about position Tyr139 to about position Ser141 of the mature human factor B protein (SEQ ID NO: 30), to an epitope of human factor B that includes at least a portion of the sequence comprising from about position Glu182 to about position Ser185 with respect to the mature human factor B protein (SEQ ID NO: 30), to an epitope of factor B that includes at least a portion of human factor B (SEQ ID NO: 30) comprising any one or more of the following positions or their equivalent positions in a non-human factor B sequence: Ala137, Tyr139, Cys 140, Ser141, Glu182, Gly184, or Ser185, or to an epitope of factor B that includes at least a portion of the equivalent positions with respect to non-human animal species. In another aspect, the epitope is within or containing a part of portion of the third SCR domain of factor B that includes all or substantially all of (at least five, six, or seven of) the following amino acid positions of SEQ ID NO: 30, or their equivalent positions in a non-human factor B sequence: Ala137, Tyr139, Ser141, Glu182, Ser185, Thr189, Glu190, and Ser192.

One of skill in the art can readily align the sequence of human factor B with the sequence of factor B from another animal species and determine the positions of the SCR regions and the specific portions of the third SCR regions corresponding to the amino acid positions above. For example, two specific sequences can be aligned to one another using BLAST 2 sequence as described in Tatusova and Madden, (1999), "Blast 2 sequences—a new tool for comparing protein and nucleotide sequences", *FEMS Microbiol. Lett.* 174:247-250, which is incorporated herein by reference in its entirety.

As used herein, the term "selectively binds to" refers to the specific binding of one protein to another (e.g., an antibody, antigen-binding fragment thereof, or binding partner to an antigen), wherein the level of binding, as measured by any standard assay (e.g., an immunoassay), is statistically significantly higher than the background control for the assay. For example, when performing an immunoassay, controls typically include a reaction well or tube that contains antibody or antigen binding fragment alone (i.e., in the absence of antigen), wherein an amount of reactivity (e.g., non-specific binding to the well or tube) by the antibody or antigen-binding fragment thereof in the absence of the antigen is considered to be background signal. Binding can be measured using a variety of methods standard in the art, including, but not limited to, Western blot, immunoblot, enzyme-linked immunosorbent assay ("ELISA"), radioimmunoassay ("RIA"), immunoprecipitation, surface plasmon resonance, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS"), and flow cytometry.

As used herein, "treating" or "to treat" a disease is defined as administering a humaneered variant of mAb 1379 as described above, such as TA101-1, TA102-4, and TA103-2, or antigen-binding fragments thereof, with or without other therapeutic agents, in order to palliate, ameliorate, stabilize, reverse, slow, delay, prevent, reduce, or eliminate either the disease or a symptom of a disease, or to retard or stop the progression of a disease or a symptom of a disease. An "effective amount" of a composition is an amount sufficient to treat a disease.

As used herein, "to inhibit" the alternative complement pathway in an individual refers to inhibiting the expression and/or the biological activity of at least one protein that is part of the alternative complement pathway. Such proteins include, but are not limited to, factor B, factor D or properdin. To "selectively" inhibit the alternative complement pathway means that the method of the present invention preferentially or exclusively inhibits the alternative complement pathway, but does not inhibit or at least does not substantially inhibit other pathways for complement activation, including the classical complement pathway or the lectin pathway. For example, the humaneered factor B antibodies and antigen-binding fragments thereof of the present invention are one example of a reagent that selectively inhibits the alternative complement pathway. This definition applies to other methods described herein wherein the alternative complement pathway is selectively inhibited.

An "individual" is a vertebrate, preferably a mammal, more preferably a human. Mammals include, but are not limited to, farm animals, sport animals, pets, primates, mice and rats. In some embodiments, the individual is human. In some embodiments, the individual is an individual other than a human. In some embodiments, the individual is an animal model for the study of a disease in which the alternative complement pathway is implicated. Individuals amenable to treatment include those who are presently asymptomatic but who are at risk of developing a symptomatic disorder in which the alternative complement pathway plays a role, or in which activation of the alternative complement pathway plays a role.

General reference to "the composition" or "compositions" includes and is applicable to compositions of the invention.

As used herein, the singular forms "a," "an," and "the" include the plural references unless clearly indicated otherwise. For example, the term "a $V_H$-region" includes one or more $V_H$-regions.

Reference to "about" a value or parameter herein includes and describes embodiments that are directed to that value or parameter per se. For example, description referring to "about X" includes description of "X."

It is understood that aspects and embodiments of the invention described herein include "consisting" and/or "consisting essentially of" aspects and embodiments.

1. Introduction

Antibody Humaneering™ generates engineered human antibodies with variable region ("V-region") sequences close to the human germ-line sequences while retaining the binding specificity and affinity of a reference antibody. See, e.g., U.S. Patent Publication No. US 2005/0255552 A1; and U.S. Patent Publication No. US 2006/0134098 A1. The process identifies the minimal sequence information required to determine antigen-binding specificity from the V-region of a reference antibody and transfers that information to a library of partial human V-region gene sequences to generate an epitope-focused library of human antibody V-regions. Members of the library are expressed as antibody Fab' fragments using a microbial-based secretion system. The library is then screened for antigen-binding Fab' fragments using a colony lift binding assay. Positive clones are further characterized to identify those with the highest binding affinity for the target antigen. The resulting engineered human Fab' fragments retain the binding specificity of the parent murine antibody, and preferably have equivalent or higher binding affinity for antigen than the parent antibody. Preferably, the engineered Fab' fragments also have heavy and light chain V-regions with a high degree of amino acid sequence identity compared to the closest human germline antibody genes.

The minimum binding specificity determinant ("BSD") required to generate the epitope-focused library is typically represented by a sequence within CDR3 of the antibody heavy chain ("$CDR_H3$") and a sequence within CDR3 of the antibody light chain ("$CDR_L3$"). In some cases, the epitope-focused library is constructed from human V-segment sequences (the "V-segment" contains FR1-CDR1-FR2-CDR2-FR3) linked to the unique region at the junction of CDR3 and FR4 containing the BSD and human germ-line joining segment ("J-segment") sequences. See U.S. Patent Publication No. US 2005/0255552 A1. Alternatively, the human V-segment libraries can be generated by sequential cassette replacement in which only part of the murine V-segment is initially replaced by a library of human sequences. The identified human "cassettes" supporting antigen binding in the context of residual murine sequences are then recombined in a second library screen to generate completely human V-segments. See U.S. Patent Publication No. US 2006/0134098 A1. In each case, paired heavy and light chain CDR3-FR4 segments containing specificity determinants from the reference antibody are used to constrain the binding specificity so that antigen-binding Fab' fragments obtained from the library retain the epitope specificity of the starting antibody (i.e., mAb 1379).

Additional maturational changes may be introduced in the CDR3 regions of each chain during library construction in order to identify antibodies with optimal binding kinetics.

The resulting humaneered antibodies have V-segment sequences derived from the human sequence libraries, retain the short BSD sequence from within the $V_L$ and $V_H$ chain CDR3 regions, and have human germline FR4 regions.

Cassette replacement was successfully used for the humaneering of mAb 1379. A number of Fab' fragments with high affinity for factor B were identified by this approach. Three humaneered Fab' fragments with higher affinity for factor B than the reference murine antibody (i.e., mAb 1379) were identified.

2. Methods 2.1 Cloning of murine V-Regions from the hybridoma producing mAb 1379

The murine V-regions were cloned from the hybridoma producing mAb 1379 as follows. First, hybridoma cells were cultured according to established procedures. The cells were then collected and messenger RNA ("mRNA") was extracted from the cell pellet by standard procedures known to one skilled in the art. First strand complementary DNA ("cDNA") was generated from the purified mRNA by primer extension with poly-deoxythymidine ("poly-dT") primer extension using reverse transcriptase, according to standard methods known to one skilled in the art. The first strand cDNA was then used as template for amplification of the antibody V-region sequences using degenerate primers according to standard procedures described in detail by Chardès, T., et al., "Efficient amplification and direct sequencing of mouse variable regions from any immunoglobulin gene family," *FEBS Lett.* 452(3):386-394 (1999), which is incorporated herein by reference. cDNA from the heavy chain variable region ("$V_H$") and the light chain variable region V-kappa ("$V_\kappa$") region was sequenced and checked for identity to amino-terminal peptide sequence data generated by Taligen. V-regions were cloned as Fab' fragments and expressed in *Escherichia coli* ("*E. coli*") from proprietary KaloBios expression vectors. The purified Fab' protein was shown to bind purified factor B protein in an enzyme-linked immunosorbent assay ("ELISA") performed according to standard methods.

2.2 Fab' Purification

Fab' fragments were expressed in *E. coli* using proprietary KaloBios protein expression vectors. Bacteria were cultured at 37° C. in 2×YT medium (16 g Bacto-tryptone, 10 g Bacto-yeast extract, and 5 g NaCl per liter of distilled, deionized water ("dd$H_2O$")) to an optical density of 0.6 absorbance units measured at a wavelength of 600 nm. Protein expression was induced using isopropyl-β-thiogalactopyranoside ("IPTG") for 3 hours at 33° C. The appropriate IPTG concentration to obtain optimal expression of the desired protein is determined empirically using methods known to one skilled in the art, and typically varies between 0.01 mM to 5.0 mM. Assembled Fab' fragments were obtained from periplasmic fractions and purified by affinity chromatography over Streptococcal Protein G columns (HiTrap™ Protein G HP columns; purchased from GE Healthcare, Piscataway, N.J.) according to standard methods known to one skilled in the art. Fab' fragments were bound to the column in 20 mM sodium phosphate, pH=7.0, eluted in 0.1 M glycine at ~pH=2.0, and immediately adjusted to neutral pH (~7.0) with an appropriate volume of 1 M Tris-HCl at pH=9.0, all according to the manufacturer's instructions. The purified Fab' fragments were then dialyzed against phosphate-buffered saline ("PBS") at pH=7.4 (1×PBS=137 mM NaCl, 2.7 mM KCl, 10 mM $Na_2HPO_4$, and 2 mM $KH_2PO_4$; note that PBS lacks $Ca^{2+}$ and $Mg^{2+}$).

2.3 Enzyme-Linked Immunosorbent Assay ("ELISA")

Taligen provided 3 mg purified recombinant human factor B. Typically, 50 ng of purified recombinant factor B was adsorbed to the wells of a 96-well microtiter plate overnight at 4° C. The plate was blocked with a solution of 5% (w/v) powdered non-fat milk in PBST (137 mM NaCl, 2.7 mM KCl, 10 mM $Na_2HPO_4$, 2 mM $KH_2PO_4$, and 0.1% (v/v) Tween-20™). Purified humaneered Fab' fragments or the reference Fab' ("TA10") were diluted in 1×PBS. Fifty microliters of antibody fragment were added to each well of the microtiter plate. After one hour at 33° C., the wells of the microtiter plate were rinsed three times with PBST. Next, fifty microliters of anti-human κ chain antibody conjugated to horseradish peroxidase ("HRP")(Sigma-Aldrich, St. Louis, Mo.) diluted to 0.1 ng/ml in PBST was added to each well, and the plate was incubated forty minutes at 33° C. The wells of the microtiter plate were then washed three times with PBST, once with 1×PBS. Then 100 μl TMB (3,3',5,5'-tetramethylbenzidene) substrate (Sigma) was added to each well, and the plate was incubated for approximately 5 minutes at room temperature (~25° C.). Finally, the reactions were stopped by addition of 100 μl 0.2 N sulfuric acid ($H_2SO_4$) to each well. The plate was read in a spectrophotometer at a wavelength of 450 nm.

2.4 Colony Lift Binding Assay

Humaneered Fab' fragment libraries were screened using nitrocellulose filters coated with recombinant human factor B, essentially as described in Example 5 of U.S. Patent Publication No. US 2005/0255552 A1, which is incorporated herein by reference. See also U.S. Patent Publication No. US 2006/0134098 A1.

Briefly, antibody libraries were transformed into a suitable bacterial host, such as the *E. coli* strain TOP10. The transformed bacterial cells are plated onto plates containing 2×YT agar (16 g pancreatic digest of casein, 10 g yeast extract, 5 g NaCl, and 15 g agar per liter) (Difco™, Becton Dickinson, Franklin Lakes, N.J.) and an appropriate selection agent (i.e., an antibiotic selected based on the particular protein expression vector used to construct the library). Plating efficiency can be adjusted to produce discrete bacterial colonies while maximizing the number of colonies per plate. At optimal density, a 10 cm diameter plate would contain ~4000 colonies, a 15 cm diameter plate would contain ~10,000 colonies, and a 25 cm diameter plate would contain ~50,000 colonies.

Nitrocellulose filters of 8.2 cm diameter, 13.2 cm diameter, or 20 cm diameter (Whatman® Schleicher & Schuell® Protran® BA85 nitrocellulose filters) (Sigma Aldrich, St. Louis, Mo.) were pre-coated with antigen (i.e., human factor B) in PBS at an empirically determined concentration (typically between 0.5 µg/ml and 20 µg/ml). The volume of coating solution varied depending on the filter size, with 4 ml used for the 8.2 cm diameter filters, 8 ml used for the 13.2 cm diameter filters, and 20 ml used for the 20 cm diameter filters. The filters were placed face down in the antigen-PBS solution for 2-3 hours at 33° C., with occasional agitation. The filters were then rinsed once with excess PBS and blocked with a 5% (w/v) solution of non-fat dry milk in PBS for 2 hours at 25° C. with agitation. The filters were then drained, rinsed once in PBS+0.1% Tween-20™ ("TBST") and twice in 2×YT liquid medium supplemented with selection agent (i.e., an appropriate antibiotic) and transcription inducer (i.e., IPTG). The filters were then drained and placed on 2×YT agar plates supplemented with the appropriate antibiotic and IPTG (the "expression plates").

Uncoated dry nitrocellulose filters of the appropriate size were placed facedown on the plates containing the *E. coli* library expressing the desired population of antibody fragments. Once the filters were visibly wet (~20-30 seconds), the filters were quickly lifted and placed colony side up onto a coated filter on an expression plate. The filters are marked to indicate the appropriate plate and orientation for ease of subsequent identification.

The expression plates covered with nitrocellulose filter "sandwiches" were placed at 33° C. for 12-16 hours. During that time, the bacterial colonies expressed and secreted the antibody fragments, which then diffused through the first nitrocellulose filter containing the colony lifts onto the antigen-coated filter beneath. Antibody fragments capable of binding the target antigen (i.e., human factor B) were retained on the antigen filter.

Antigen-bound antibody fragments were detected with immunological methods. Briefly, the filters containing antigen-bound antibody fragments were removed from the expression plates, washed 3 times for 5 minutes each in PBST, and blocked for 1.5 hours at 25° C. in a solution of 5% (w/v) non-fat dry milk in PBST. The antigen-antibody fragment complexes retained on the filters were then incubated with an appropriate primary antibody (e.g., goat anti-κ antibody conjugated to HRP, and the like), followed if necessary by an appropriate secondary antibody. Other standard immunological detection methods may be used, including biotin/streptavidin, as well as other detection methods, including various fluorescent labels. The filters were then washed 4 times for 10 minutes each in PBST, incubated in peroxidase substrate solution, and exposed to light-sensitive photographic film. Alternatively, various imaging systems can be used to visualize the positive colonies, such as the Typhoon (Amersham Biosciences, GE Healthcare, Piscataway, N.J.) or the FX-Pro PhosphorImager (Biorad, Hercules, Calif.). The images on the film are then aligned to the appropriate plate, and positive colonies (i.e., those producing antibody fragments capable of binding the desired antigen (e.g., human factor B)) were picked, inoculated into 2×YT medium plus selection agent, and further analyzed through subsequent rounds of CLBA using substantially the same procedures.

2.5 Affinity Measurements

Binding kinetics of the Fab' fragments were analyzed using a FortéBio® Octet® biosensor (FortéBio, Inc., Menlo Park, Calif.). Recombinant human factor B was biotinylated with the EZ-link biotinylation system (Pierce Biotechnology, Rockford, Ill.) according to the manufacturer's instructions. The antigen was then coupled to neutravidin-coated sensors (FortéBio, Inc., Menlo Park, Calif.) according to the manufacturer's instructions. Fab' binding was then monitored in real time using bio-layer interferometry analysis and software provided by the manufacturer. Antigen binding affinities were calculated for the tested Fab' fragments based on the measured association ("$K_{assoc}$") and dissociation ("$K_{dissoc}$") constants. Preferably humaneered antibodies or antibody fragments with equilibrium dissociation constants the same or higher than that of the reference antibody (i.e., mAb 1379) or antibody fragment (i.e., TA10).

3. Results 3.1 Cloning and Expression of V-Regions from the Hybridoma Producing mAb 1379

3.1.1. $V_H$ and $V_\kappa$ Chain Amplification from First Strand cDNA

Variable regions from the antibody light chain (κ isoform) and heavy chain were amplified from first strand cDNA using fifteen $V_H$ and eighteen $V_\kappa$ primer sets. Each $V_H$ primer set contained one of fifteen degenerate forward primers specific for the known murine heavy chain families paired with an appropriate reverse primer specific for a constant domain from one of the four common murine isoforms of the γ heavy chain (i.e., the murine $\gamma_1$ isoform). See, e.g., Chardès et al., *FEBS Lett.* 452(3):386-394 (1999). Each $V_\kappa$ primer set contained one of eighteen degenerate forward primers specific for the known murine κ families paired with a reverse primer specific for a constant domain from the κ isoform of the murine light chain. See, e.g., Chardès et al., *FEBS Lett.* 452 (3):386-394 (1999).

Two primer sets produced PCR products for the heavy chain, and two primer sets produced PCR products for the light chain. Although the degenerate forward primers were designed to hybridize to the relatively conserved signal sequences of each murine heavy and light chain family, not every primer pair amplifies the expected product because germline signal sequences vary. In addition, immunoglobulin loci frequently contain pseudogenes that can produce a product of the expected size yet do not encode the predicted open reading frame, as was the case with the product produced by the $V_\kappa 10$ primer pair (see paragraph [0065] below). FIG. 1 is an agarose gel stained with ethidium bromide to show double-stranded cDNA products amplified from first strand cDNA prepared from mRNA isolated from the hybridoma producing mAb 1379. Primer pairs $V_\kappa 4$ (SEQ ID NO: 1 (forward primer) and SEQ ID NO: 2 (reverse primer)) and $V_\kappa 10$ (SEQ ID NO: 3 (forward primer) and SEQ ID NO: 4 (reverse primer)) produced products of the expected size from the antibody light chain. Primer pairs $V_H 6$ (SEQ ID NO: 5 (forward primer) and SEQ ID NO: 6 (reverse primer)) and $V_H 7$ (SEQ ID NO: 7 (forward primer) and SEQ ID NO: 8 (reverse primer)) produced products of the expected size from the antibody heavy chain.

3.1.2. Murine V-Region Amino Acid Sequences

The $V_H$ and $V_\kappa$ cDNA clones obtained as described in paragraph [0063] and [0064] above were sequenced by standard methods to verify the correct products were obtained. The V-region sequences obtained are shown in FIG. 2. CDR sequences are underlined. Two glutamine residues that differ from the murine germline sequence corresponding to the original mAb 1379 antibody are shown shaded grey. The products obtained with the $V_H6$ (SEQ ID NO: 10) and $V_H7$ (SEQ ID NO: 11) primer sets were identical in amino acid sequence. The $V_\kappa 10$ product was amplified from a cDNA containing a rearrangement or frameshift that disrupted the protein open reading frame, and so is not shown. The $V_\kappa 4$ (SEQ ID NO: 9) product contained the expected open reading frame. One of the selected murine $V_H$ clones was then attached to a human $IgG_1$ $C_H1$-region, and the murine $V_\kappa 4$ clone was attached to a human $C_\kappa$-region to make the reference Fab' (i.e., TA10). The humaneered Fab' variants also comprised human constant region sequences.

3.1.3. Comparison of Cloned V-Region and Amino-Terminal Amino Acid Sequences Provided by Taligen The amino-terminal amino acid sequences of mAb 1379 were then compared to the same portion of the cloned $V_H$ and $V_\kappa$ sequences. FIG. 3 shows the aligned portions of the sequences, first from the $V_H$ chain (top, compare "1379H" (SEQ ID NO: 31) to "TA-$V_H6$" (SEQ ID NO: 33)), then from the $V_H$ and $V_\kappa$ chain (bottom, compare "1379L" (SEQ ID NO: 32) to "TA-$V_\kappa 4$" (SEQ ID NO: 34)). The amino-terminal sequences of mAb 1379 and the cloned sequences were identical apart from four residues (shown shaded grey). Those differences resulted from errors introduced during the Edman-degradation reaction used to obtain the amino-terminal peptide sequences of mAb 1379.

3.1.4. Confirmation of Factor B Binding Activity of the Cloned V-Regions by ELISA Next, the ability of the cloned $V_H$ and $V_\kappa$ sequences to bind factor B was assayed. The cloned $V_H$- and $V_\kappa$-regions were expressed in bacteria as Fab' fragments, purified, and tested for binding to factor B in a dilution ELISA. FIG. 4 compares factor B binding of the cloned Fab' TA003 to that of a Fab' derived from mAb1379. As expected, both the cloned Fab' and murine Fab produced binding curves that were dependent on both antibody and antigen concentration.

3.2 Humaneering of mAb 1379 V-Regions 3.2.1. Library Construction and V-Region Cassettes Epitope-focused libraries were constructed by linking human V-segment library sequences (isolated from spleen) to the unique CDR3-FR4 region containing the BSD and human germ-line J-segment sequences. These "full-length" libraries were used as a base for construction of "cassette" libraries in which only part of the murine V-segment is initially replaced by a library of human sequences. The cassettes for both $V_H$ and $V_\kappa$ chains were made by bridge PCR with overlapping common sequences within the FR2 region. In this way, "front-end" and "middle" human cassette libraries were constructed for human $V_H1$, $V_H3$, and $V_\kappa IV$ isotypes. Typically, approximately 10,000 unique Fab' clones are screened between the "front-end" and "middle" human cassette libraries to identify a pool of candidate antibody fragments that bind the desired antigen (i.e., human factor B) with a binding affinity at least equal to or greater than the binding affinity of a reference antibody or antibody fragment (i.e., mAb 1379 or TA10).

Human "front-end" and "middle" cassettes which supported binding to factor B were identified by colony-lift binding assay and ranked according to affinity in ELISA and FortéBio® analysis. Colony-lift binding assays were performed as described above, essentially as in Example 5 of U.S. Patent Publication No. US 2005/0255552 A1, which is incorporated herein by reference. Pools of the highest affinity "cassettes" (with antigen-binding affinity preferably equal to or greater than TA10, the reference Fab' derived from mAb 1379) were then recombined via the common FR2 sequences in a second library screen to generate completely human V-segments.

After identification of a pool of high affinity, fully humaneered Fab' fragments, affinity maturation libraries were built. The common BSD sequences of a panel of humaneered Fab' clones were randomly mutated using degenerate PCR primers to generate libraries. These mutagenic libraries were screened by colony lift binding assay. The selected Fab' fragments were ranked for binding affinity with ELISA and FortéBio® analysis. Mutations which supported equal or improved binding affinity for antigen compared to the TA10 reference Fab' fragment were identified.

In some cases, the humaneering process results in isolation of a pool of fully humaneered Fab' fragments with the same or very similar binding affinities for the target antigen. In such cases, the pool of Fab' fragments is sequenced and compared to the closest human germline $V_H$- and $V_L$- (i.e., $V_\kappa$-) region sequences, and the humaneered antibody fragments with the highest degree of amino acid sequence identity to the human germline are selected for further analysis. The higher the degree of amino acid sequence identity to the human germline sequence, the less immunogenic a humaneered antibody or antibody fragment will be, and thus, the less likely it will be to provoke an immune or inflammatory response, or to increase an existing immune or inflammatory response. Because the humaneered variants of mAb 1379 may be used to treat conditions in which an immune or inflammatory response has already been triggered (i.e., conditions in which activation of the alternative complement pathway plays a role, such as airway hyperresponsiveness and the like), it is essential that the immunogenicity of the humaneered variants be reduced as much as possible. Furthermore, because administration of proteins into the lung (i.e., by inhalation, as contemplated herein) is more likely to induce an immune response than other routes of administration, it is even more important that the humaneered anti-factor B variants be minimally immunogenic.

Thus, it is desirable to isolate humaneered variants with the highest possible degree of amino acid sequence identity to the closest human germline sequences (for variants derived from mAb 1379, the closest human germline sequences are $V_\kappa IV$-B3/$J_\kappa 2$ (SEQ ID NO: 12) and $V_H 1$-02/$J_H 4$ (SEQ ID NO: 13)). Preferably, the humaneered variants have $V_H$- and $V_\kappa$-region amino acid sequences at least 80% identical to the closest human germline $V_H$- and $V_\kappa$-region amino acid sequences, more preferably at least 85% identical to the closest human germline $V_H$- and $V_\kappa$-region amino acid sequences, still more preferably at least 90% identical to the closest human germline $V_H$- and $V_\kappa$-region amino acid sequences, and even more preferably at least 95% identical to the closest human germline $V_H$- and $V_\kappa$-region amino acid sequences.

Preferably, a humaneered antibody variant will have a binding affinity equal to or greater than the reference antibody or antibody fragment, and would further comprise $V_H$- and $V_\kappa$-regions having amino acid sequences 80% identical to the closest human germline sequence, 85% identical to the closest human germline sequence, 90% identical to the closest human germline sequence, or 95% identical to the closest human germline sequence. It is not always possible to humaneer antibody or antibody fragment variants that share both those characteristics, however.

Figure 5:
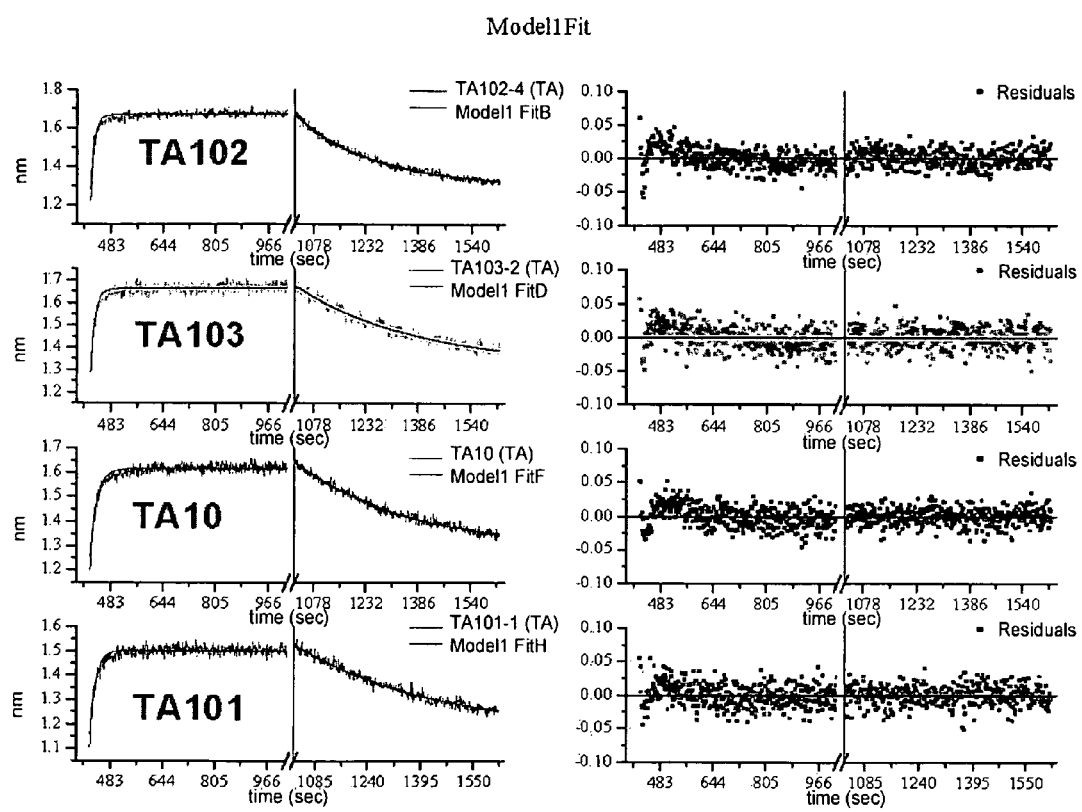
FIG. 5 shows the kinetics of Fab' fragment binding to recombinant human factor B analyzed with the FortéBio® Octet® system by bio-layer interferometry.

3.2.2. Binding affinity of Fab' fragments for human factor B using FortéBio® Octet® Analysis Fully humaneered Fab' fragments were isolated by colony lift binding assays and confirmed as factor B binders by ELISA. Humaneered Fab' fragments showing strong positive signals by ELISA were purified and further characterized in comparison to the reference Fab' fragment TA10, which has murine V-region sequences from mAb 1379. Kinetics of Fab' fragment binding to recombinant human factor B were analyzed with the FortéBio® Octet® system by bio-layer interferometry, providing real time label-free monitoring of protein-protein interactions. Representative kinetic analyses are shown in FIG. 5. Measured association ($K_{assoc}$) and dissociation ($K_{dissoc}$) constants, and calculated equilibrium dissociation constants ($K_D = K_{dissoc}/K_{assoc}$) (i.e., binding affinity), are shown in Table 1.

TABLE 1

Kinetic analysis of humaneered antibodies compared to a reference antibody.

| TrackingID | TA102-4 | TA103-2 | TA10 (Reference) | TA101-1 |
|---|---|---|---|---|
| Concentration (M) | $1 \times 10^{-7}$ | $1 \times 10^{-7}$ | $1 \times 10^{-7}$ | $1 \times 10^{-7}$ |
| $K_{dissoc}$ (1/sec) | $4.37 \times 10^{-3}$ | $2.80 \times 10^{-3}$ | $2.96 \times 10^{-3}$ | $2.33 \times 10^{-3}$ |
| $K_{dissoc}$ (error) | $1.03 \times 10^{-4}$ | $1.29 \times 10^{-4}$ | $1.07 \times 10^{-4}$ | $1.27 \times 10^{-4}$ |
| $K_{assoc}$ (1/(M·sec)) | $8.10 \times 10^{-5}$ | $7.50 \times 10^{-5}$ | $4.52 \times 10^{-5}$ | $5.14 \times 10^{-5}$ |
| $K_D$ (M) | $5.40 \times 10^{-9}$ | $3.73 \times 10^{-9}$ | $6.55 \times 10^{-9}$ | $4.53 \times 10^{-9}$ |

Clearly, all three humaneered antibody fragments have equilibrium dissociation constants equal to or better than the TA10 reference antibody fragment.

3.3 Sequence Analysis of Humaneered Fab' Fragments 3.3.1. Alignment of Reference and Humaneered Fab' Amino Acid Sequences After kinetic characterization, the three humaneered antibody isolates were sequenced. Amino acid sequences derived from the $V_\kappa$- and $V_H$-region sequences of antibody isolates TA101-1 (SEQ ID NOS: 16 and 17), TA102-4 (SEQ ID NOS: 18 and 19), and TA103-2 (SEQ ID NOS: 20 and 21) were compared to the corresponding sequences from the reference antibody TA10 (SEQ ID NOS: 14 and 15) and from the closest human germline light and heavy chain variable domain genes ("$V_\kappa$-" and "$V_H$-gene") and joining segments ("J-segment") (human $V_\kappa IV$-B3/$J_\kappa 2$ (SEQ ID NO: 12) and $V_H 1$-02/$J_H 4$ (SEQ ID NO: 13)). Aligned sequences are shown in FIG. 6. The sequences CDR1, CDR2, and CDR3 are boxed and labeled accordingly. Amino acid residues that differ from the corresponding germline position (excluding the CDR3 BSD sequence) are shaded in grey. Affinity maturation changes to the CDR3 amino acid sequences of humaneered variants TA101-1, TA102-4, and TA103-2 are shaded in grey and shown in boldface type.

In certain embodiments, the $V_H$-region sequences of TA101-1 (SEQ ID NO: 35), TA102-4 (SEQ ID NO: 36), and TA103-2 (SEQ ID NO: 37) are modified to replace the amino-terminal glutamine (Q) residue of the humaneered anti-factor B variants with a glutamic acid (E) residue as found in the reference antibody (TA10) and the original mAb 1379. This change prevents cyclization of the glutamine (Q) residue and promotes a more uniform final product when manufacturing the humaneered variants. Although the closest human germline gene ($V_H 1$-02/$J_H 4$ (SEQ ID NO: 13)) also has a glutamine (Q) residue at its amino terminus, this conservative amino acid substitution likely has minimal impact on immunogenicity of the variants.

3.3.2. Percent Identity to Human Germline Sequences

Finally, the $V_H$-region and $V_\kappa$-region amino acid sequences derived from the TA101-1, TA102-4, and TA103-2 isolates and the TA10 reference antibody were compared to a single human germline antibody sequence across the V-region, excluding the CDR3BSD sequences. Table 2 shows the percent amino acid identity to the germline sequence for each.

| Clone | $V_\kappa$ % identity (aligned to $V_\kappa IV$) | $V_H$ % identity (aligned to $V_H 1$-02) | Total % identity across V-region (excluding CDR3) |
|---|---|---|---|
| TA10 reference | 70.4% | 84.9% | 77.7% |
| TA101-1 | 96.2% | 96.3% | 96.25% |
| TA102-4 | 97.1% | 96.3% | 96.7% |
| TA103-2 | 95.3% | 96.3% | 95.8% |

Clearly, the $V_\kappa$- and $V_H$-regions of all three humaneered Fab' fragments share high amino acid sequence identity to the human germline sequence, with percent identities of about 96% compared to about 78% for the reference Fab' fragment, TA10.

4. Discussion

Cassette replacement was used successfully for humaneering of mAB 1379. Partial V-region cassettes isolated from a human library were recombined to form the final engineered human V-regions for each of the heavy and light chains.

The amino acid sequences of the V-regions from the Fab' fragment clones are provided above. V-segment sequences were isolated by recombination of two $V_H$ cassettes and two $V_\kappa$ cassettes for each Fab' fragment (a "front-end" and a "middle" cassette for each of the $V_H$ and $V_\kappa$ polypeptides). Kinetic analysis using the FortéBio® Octet® biosensor identified three Fab' fragments (TA101-1, TA102-4, and TA103-2) with higher binding affinities than the reference Fab' fragment. This increased binding affinity resulted from an improved off-rate in the three humaneered variants (i.e., TA101-1, TA102-4, and TA103-2) when compared to the reference molecule. Thus, it may also be desirable to screen for variants based upon increased off-rates ($K_{dissoc}$) and/or increased binding affinities, as well as % amino acid sequence identity between the humaneered $V_H$ and $V_\kappa$ polypeptides and the closest human germline $V_H$ and $V_\kappa$ sequences.

Each of the three Fab' fragment clones has a heavy chain variable region ($V_H$) with a high degree of amino acid sequence identity to the human $V_H 1$-02 germ-line gene. The $FR_H 4$ segment is provided by the human germ-line $J_H 4$ sequence.

The light chain V-segments are closest to the $V_\kappa IV$-B3 germline gene. The $FR_L 4$ the same is provided by the human germ-line $J_\kappa 2$ segment. The humaneered Fab' fragment $V_H$ and $V_L$ regions show greater than 96% amino acid sequence identity to the closest corresponding human germ-line sequence cassettes outside the unique CDR3 regions.

5. Formulations, Compositions, and Methods Relating to Certain Embodiments of the Invention One aspect of the present invention generally relates to compositions and methods for selectively inhibiting activation of the alternative complement pathway in an animal that has, or is at risk of developing, a condition or disease in which activation of the alternative complement pathway contributes to the condition or disease, exacerbates at least one symptom of the condition or disease, or causes the condition or disease.

5.1 Methods Relating to Certain Embodiments of the Invention

Certain embodiments of the present invention related to methods of treating diseases or disorders in which activation of the alternative complement pathway plays a role. Such methods involve administering a humaneered variant of mAb 1379 as described above, such as TA101-1, TA102-4, and TA103-2, or antigen-binding fragments thereof, to an individual that has, or is at risk of developing, a disease in which activation of the alternative complement pathway plays a role. In one aspect, the humaneered antibody variants and antigen-binding fragments thereof are administered by a route selected from the group consisting of: oral, nasal, topical, inhaled, intratracheal, transdermal, rectal and parenteral routes. In another aspect, the humaneered antibody variants and antigen-binding fragments thereof are administered with a pharmaceutically acceptable carrier selected from the group consisting of: a dry, dispersible powder; anhydrous ethanol; small capsules; liposomes; a nebulized spray; and an injectable excipient. In another aspect, the humaneered variants and antigen-binding fragments thereof are administered in a carrier or device selected from the group consisting of: anhydrous ethanol; a dry powder inhalation system; ultrasonic inhalation system; a pressurized metered dose inhaler; and a metered solution device. In another aspect, the humaneered antibody variants and antigen-binding fragments thereof are administered in an amount effective to treat the disease or disorder in which activation of the alternative complement pathway plays a role. In still other aspects, the humaneered antibody variants and antigen-binding fragments thereof are administered alone, or in combination with another agent selected from the group consisting of: corticosteroids, β-agonists (long or short acting), leukotriene modifiers, antihistamines, phosphodiesterase inhibitors, sodium cromoglycate, Nedocromil, theophylline, cytokine antagonists, cytokine receptor antagonists, anti-IgE, and inhibitors of T cell function.

Still other embodiments of the present invention relate to a method to reduce or prevent airway hyperresponsiveness (AHR) or airway inflammation in an individual. The method includes the step of administering a humaneered variant of mAb 1379 as described above, such as TA101-1, TA102-4, and TA103-2, or antigen-binding fragments thereof, to an individual that has, or is at risk of developing, airway hyperresponsiveness associated with inflammation or airway inflammation. In one aspect, the humaneered variant of mAb 1379 or antigen-binding fragment thereof is administered by a route selected from the group consisting of oral, nasal, topical, inhaled, intratracheal, transdermal, rectal and parenteral routes. In another aspect, the humaneered variant of mAb 1379 or antigen-binding fragment thereof is administered to the animal in an amount effective to measurably reduce airway hyperresponsiveness in the individual as compared to prior to administration of the antibody or antigen binding fragment. In another aspect, the humaneered variant of mAb 1379 or antigen-binding fragment thereof is administered to the individual in an amount effective to measurably reduce airway hyperresponsiveness in the individual as compared to a level of airway hyperresponsiveness in a population of individuals having inflammation wherein the antibody or antigen binding fragment was not administered. In another aspect, the humaneered variant of mAb 1379 or antigen-binding fragment thereof is administered with a pharmaceutically acceptable carrier selected from the group consisting of: a dry, dispersible powder; anhydrous ethanol; small capsules; liposomes; a nebulized spray; and an injectable excipient. In another aspect, the humaneered variant of mAb 1379 or antigen-binding fragment thereof is administered in a carrier or device selected from the group consisting of: anhydrous ethanol; a dry powder inhalation system; ultrasonic inhalation system; a pressurized metered dose inhaler; and a metered solution device.

In yet another aspect, the humaneered variant of mAb 1379 or antigen-binding fragment thereof is administered to an individual in conjunction with an agent selected from the group consisting of: corticosteroids, β-agonists (long or short acting), leukotriene modifiers, antihistamines, phosphodiesterase inhibitors, sodium cromoglycate, Nedocromil, theophylline, cytokine antagonists, cytokine receptor antagonists, anti-IgE, and inhibitors of T cell function. In yet another aspect, the airway hyperresponsiveness or airway inflammation is associated with a disease selected from the group consisting of asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus (RSV) infection, parainfluenza virus (PIV) infection, rhinovirus (RV) infection and adenovirus infection. In one aspect, the airway hyperresponsiveness is associated with allergic inflammation. The method of the present invention can be administered, in a preferred embodiment, to mammals, and more preferably, to humans.

Another embodiment of the present invention relates to a method to reduce or prevent airway hyperresponsiveness (AHR) or airway inflammation in an individual. The method includes the step of administering a reagent that selectively inhibits the alternative complement pathway to an individual that has, or is at risk of developing, airway hyperresponsiveness associated with inflammation or airway inflammation. In certain aspects, that reagent is a humaneered variant of mAb 1379, such as TA101-1, TA102-4, and TA103-2, or antigen-binding fragments thereof.

5.2 Formulations or Compositions Relating to Certain Embodiments of the Invention Certain embodiments of the humaneered anti-factor B antibody variants of the present invention include a formulation or composition comprising an inhibitor of the alternative complement pathway and particularly, a selective inhibitor of the alternative complement pathway as described herein. The formulations or compositions can be used in any of the methods described herein and with any of the reagents described herein (e.g., the humaneered factor B antibody variants TA101-1, TA102-4, and TA103-2 or antigen-binding fragments thereof as described herein). In one embodiment, the composition is useful for reducing or preventing airway hyperresponsiveness in an animal. In another embodiment, the composition is useful for reducing or preventing ischemia-reperfusion injury in an animal. In yet another embodiment, the composition is useful for treating or preventing a condition or disease by selective inhibition of the alternative complement pathway. The formulation comprises: (a) an inhibitor of the alternative complement pathway as described herein; and (b) a pharmaceutically acceptable carrier.

In one embodiment, the formulation or composition can include one or more additional agents, such as an anti-inflammatory agent suitable for reducing inflammation in an animal that has, or is at risk of developing, airway hyperresponsiveness, and particularly, airway hyperresponsiveness associated with inflammation. The anti-inflammatory agent can be any anti-inflammatory agent suitable for use in reducing inflammation in a patient that has an inflammatory condition associated with airway hyperresponsiveness, including, but not limited to: corticosteroids, (oral, inhaled and injected), β-agonists (long or short acting), leukotriene modifiers (inhibitors or receptor antagonists), cytokine or cytokine receptor antagonists, anti-IgE antibodies, phosphodiesterase inhibitors, sodium cromoglycate, nedocrimal, theophylline, and inhibitors of T cell function. Particularly preferred anti-inflammatory agents for use in the present formulation include, corticosteroids, leukotriene modifiers, and cytokine or cytokine receptor antagonists.

In another embodiment, the formulation or composition can include one or more additional agents, such as an additional agent suitable for preventing or reducing ischemia-reperfusion injury in an animal. Such agents include, but are not limited to, anti-inflammatory agents; or inhibitors of oxidation and free radical damage.

In another embodiment, the formulation or composition can include one or more additional agents, such as an additional agent suitable for treatment of another disease or condition associated with activation of the alternative complement pathway.

According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein the alternative complement pathway can be inhibited. In one preferred embodiment, when the patient has or is at risk of developing airway hyperresponsiveness and/or airway inflammation, a suitable in vivo site is preferably in the lung tissue or airways. Other preferred in vivo sites include other tissues or organs where conditions associated with the alternative complement pathway may be centered. In another preferred embodiment, a suitable in vivo site is any site where ischemia-reperfusion injury occurs, such as in the heart or pulmonary system, central nervous system, limbs or digits, internal organs (e.g., lung, liver or intestine), or in any transplanted organ or tissue. Preferred pharmaceutically acceptable carriers are capable of maintaining an agent used in a formulation of the invention in a form that, upon arrival of the agent at the target site in a patient, the agent is capable of acting on its target (e.g., a protein that is a component of the alternative complement pathway), preferably resulting in a therapeutic benefit to the patient.

Suitable excipients for use in the present invention include excipients or formularies that transport or help transport, but do not specifically target a composition to a cell or tissue (also referred to herein as non-targeting carriers). Examples of pharmaceutically acceptable excipients include, but are not limited to water, phosphate buffered saline ("PBS"), Ringer's solution, dextrose solution, serum-containing solutions, Hank's Balanced Salt Solution ("HBSS"), and other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzyl alcohol. Formulations of the present invention can be sterilized by conventional methods and/or lyophilized.

One type of pharmaceutically acceptable carrier includes a controlled-release formulation that is capable of slowly releasing a composition of the present invention into an animal. As used herein, a controlled-release formulation comprises an agent of the present invention in a controlled-release vehicle. Suitable controlled-release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other suitable carriers include any carrier that can be bound to or incorporated with the agent that extends that half-life of the agent to be delivered. Such a carrier can include any suitable protein carrier or even a fusion segment that extends the half-life of a protein when delivered in vivo. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of an inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

In one embodiment, an agent useful in the present methods is administered in a formulation suitable for pulmonary or nasal delivery, and particularly, aerosol delivery, also referred to herein as an aerosolized formulation. Such a route of delivery is particularly useful in the method to prevent or inhibit AHR and/or airway inflammation in a patient, but can be used in other conditions when delivery to the lung or airways is desired. In addition, these formulations are particularly useful for the delivery of antibodies. Such a formulation generally includes a carrier, and preferably, a pharmaceutically acceptable carrier. Carriers that are particularly useful for aerosol delivery according to the present invention include, but are not limited to: anhydrous ethanol; dry, dispersible powders; small capsules (e.g., microcapsules or microparticles); liposomes; injectable excipients; and nebulized sprays. Anhydrous ethanol for the delivery of proteins and peptides is described, for example, in Choi et al., *Proc. Nat'l Acad. Sci. USA* 98(20):11103-11107 (2001). Dry, dispersible powders suitable for aerosolized delivery of agents are described in detail, for example, in U.S. Pat. No. 6,165,463, incorporated herein by reference in its entirety (See also products from Inhale Therapeutic Systems, Inc., now Nektar, and Quadrant Technology). Suitable liposomes for use in aerosols include any liposome, and particularly, any liposome that is sufficiently small to be delivered by aerosol in the method of the invention. Microcapsules and microparticles are known in the art. For example, Alliance Pharmaceutical Corporation has a particle engineering technology called PulmoSphere, in which microparticles are prepared by a proprietary spray-drying process and are designed to be both hollow and porous. A product by Ventolin consists of micronized albuterol (free base) particles suspended in a mixture of CFC-based propellants. Proventil HFA contains micronized albuterol sulfate and a small percentage of an ethanol co-solvent to solubilize the stabilizing oleic acid surfactant. Incorporation of drugs into liposomes has several advantages for aerosol delivery. Because liposomes are relatively insoluble, the retention time of some drugs in the lung can be prolonged for increased efficacy. Liposomes are also taken up primarily by phagocytic cells which make them particularly suitable for delivery of certain drugs. Devices for delivery of aerosolized formulations include, but are not limited to, pressurized metered dose inhalers ("MDI"), dry powder inhalers ("DPI"), metered solution devices ("MSI"), and ultrasonic inhalers, and include devices that are nebulizers and inhalers. Various agents can be used in formulations delivered by such devices as suspension aids and solubilizers that are particularly useful for the delivery of proteins (e.g., oligolactic acid, acyl-amide acids, and mono-functionalized M-PEGS; see, e.g., McKenzie and Oliver; 2000, *Formulating Therapeutic Proteins and Peptides in Pressurized Metered Dose Inhalers For Pulmonary Delivery*, 3M Health Care Ltd., Morley Street, Loughborough, Leicesteshire LE11 1EP, UK).

A pharmaceutically acceptable carrier which is capable of targeting is herein referred to as a "targeting delivery vehicle." Targeting delivery vehicles of the present invention are capable of delivering a formulation, including an inhibitory agent, to a target site in a patient. A "target site" refers to a site in a patient to which one desires to deliver a therapeutic formulation. For example, a target site can be any cell or tissue which is targeted by an antibody of the present invention, or by direct injection or delivery using liposomes, viral vectors or other delivery vehicles, including ribozymes. A delivery vehicle or antibody of the present invention can be modified to target a particular site in an animal, thereby targeting and making use of particular compound, antibody, protein, or nucleic acid molecule at that site. Suitable modifications include manipulating the chemical formula of the lipid portion of a delivery vehicle and/or introducing into the vehicle a compound capable of specifically targeting a delivery vehicle to a preferred site, for example, a preferred cell or tissue type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Particularly useful examples include any ligands associated with the complement pathway (e.g., CR2, C3, C3d, C3dg, iC3b, C3b) or any ligands associated with the cell type, tissue type, or site in the animal to be treated. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with cells having particular charge characteristics.

One delivery vehicle useful for a variety of administration routes and agents is a liposome. A liposome is capable of remaining stable in an animal for a sufficient amount of time to deliver a nucleic acid molecule, or even a protein or antibody as described in the present invention, to a preferred site in the animal. According to the present invention, a liposome comprises a lipid composition that is capable of delivering a nucleic acid molecule, protein, or antibody as described in the present invention to a particular, or selected, site in an animal. A liposome according to the present invention comprises a lipid composition that is capable of fusing with the plasma membrane of the targeted cell to deliver its contents into a cell. Suitable liposomes for use with the present invention include any liposome. Preferred liposomes of the present invention include those liposomes typically used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule, protein or antibody of the present invention can be achieved using methods standard in the art.

In accordance with the present invention, determination of acceptable protocols to administer an agent, composition or formulation, including the route of administration and the effective amount of an agent to be administered to an animal, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). The term "ex vivo" refers to performing part of the administration step outside of the patient. Preferred routes of administration for antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, e.g., Stribling et al., *Proc. Nat'l Acad. Sci. USA* 189:11277-11281 (1992), which is incorporated herein by reference in its entirety). Carriers suitable for aerosol delivery are described above. Devices for delivery of aerosolized formulations include, but are not limited to, pressurized metered dose inhalers ("MDI"), dry powder inhalers ("DPI"), and metered solution devices ("MSI"), and include devices that are nebulizers and inhalers. Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

A preferred single dose of an agent, including proteins, small molecules and antibodies, for use in any method described herein, comprises between about 0.01 µg/kg and about 10 mg/kg body weight of an animal. A more preferred single dose of an agent comprises between about 1 µg/kg and about 10 mg/kg body weight of an animal. An even more preferred single dose of an agent comprises between about 5 µg/kg and about 7 mg/kg body weight of an animal. An even more preferred single dose of an agent comprises between about 10 µg/kg and about 5 mg/kg body weight of an animal. A particularly preferred single dose of an agent comprises between about 0.01 mg/kg and about 1 mg/kg body weight of an animal, if the agent is delivered by aerosol. Another particularly preferred single dose of an agent comprises between about 1 mg/kg and about 10 mg/kg body weight of an animal, if the agent is delivered parenterally.

In one embodiment a suitable dose of an agent of the present invention for use in any method described herein is a dose effective to inhibit the expression or activity of at least one protein in the alternative complement pathway as described herein (e.g., factor B, factor D or properdin), as compared to in the absence of the administration of the agent. Methods of measuring the expression or biological activity of a protein are known in the art and include, for example, Northern blotting, Western blotting, real time RT-PCR, and the like. In another embodiment, a suitable dose of an agent of the present invention is a dose that measurably inhibits the alternative complement pathway of the invention. Activation of complement and inhibition thereof can be measured using techniques/assays that are well-known in the art. For example, one can perform an in vitro analysis of C3 deposition on zymosan A particles as described in the examples of co-pending U.S Patent Publication No. US-2005/0260198 A1, which is incorporated herein by reference. One can also test the ability of the agent to inhibit lysis of unsensitized erythrocytes by human serum. Extrapolation of in vitro results to in vivo dosages based on these assays is within the ability of those of skill in the art.

In humans, it known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting a mouse dosage to a human dosage using alometric scaling. Essentially, a scale of dosage from mouse to human is based on the clearance ratio of a compound and the body surface of the mouse. The conversion for mg/kg is one twelfth of the "no observed adverse event level" ("NOEL") to obtain the concentration for human dosage. This calculation assumes that the elimination between mouse and human is the same, which is believed to be the case for antibodies.

Accordingly, a preferred single dose of an antibody comprises between about 1 ng/kg and about less than 1 mg/kg body weight of an animal. A more preferred single dose of an antibody comprises between about 20 ng/kg and about 600 µg/kg body weight of the animal. An even more preferred single dose of an antibody, particularly when the antibody formulation is delivered by nebulization, comprises between about 20 ng/kg and about 600 µg/kg body weight of the animal, and more preferably, between about 20 ng/kg and about 500 µg/kg, and more preferably, between about 20 ng/kg and about 400 µg/kg, and more preferably, between about 20 ng/kg and about 300 µg/kg, and more preferably, between about 20 ng/kg and about 200 µg/kg, and more preferably, between about 20 ng/kg and about 100 µg/kg, and more preferably, between about 20 ng/kg and about 50 µg/kg body weight of the animal.

Another preferred single dose of an antibody, particularly when the antibody formulation is delivered by nebulization, comprises between about 200 ng/kg and about 600 µg/kg body weight of the animal, and more preferably, between about 200 ng/kg and about 500 µg/kg, and more preferably, between about 200 ng/kg and about 400 µg/kg, and more preferably, between about 200 ng/kg and about 300 µg/kg, and more preferably, between about 200 ng/kg and about 200 µg/kg, and more preferably, between about 200 ng/kg and about 100 µg/kg, and more preferably, between about 200 ng/kg and about 50 µg/kg body weight of the animal.

Another preferred single dose of an antibody, particularly when the antibody formulation is delivered by direct inhalation from an inhaler, comprises between about 2 ng/kg and about 100 µg/kg body weight of the animal, and more preferably, between about 2 ng/kg and about 50 µg/kg, and more preferably, between about 2 ng/kg and about 10 µg/kg, and more preferably, between about 2 ng/kg and about 5 µg/kg, and more preferably, between about 2 ng/kg and about 1 µg/kg, and more preferably, between about 2 ng/kg and about 0.5 µg/kg, and more preferably, between about 2 ng/kg and about 0.25 µg/kg, and more preferably, between about 2 ng/kg and about 0.1 µg/kg body weight of the animal.

In another embodiment, the antibody is administered at a dose of less than about 500 µg antibody per milliliter of formulation, and preferably, less than about 250 µg antibody per milliliter of formulation, and more preferably, less than about 100 µg antibody per milliliter of formulation, and more preferably, less than about 50 µg antibody per milliliter of formulation, and more preferably, less than about 40 µg antibody per milliliter of formulation, and more preferably, less than about 30 µg antibody per milliliter of formulation, and more preferably, less than about 20 µg antibody per milliliter of formulation, and more preferably, less than about 10 µg antibody per milliliter of formulation, and even more preferably, between about 5 µg antibody and about 10 µg antibody per milliliter of formulation.

With more particular regard to the method of reducing or preventing airway hyperresponsiveness and/or airway inflammation or a condition or disease related thereto, a suitable single dose of an inhibitory agent to administer to an animal is a dose that is capable of reducing or preventing airway hyperresponsiveness and/or airway inflammation, or reducing at least one other symptom of a disease to be treated (e.g., asthma), in an animal when administered one or more times over a suitable time period. When the patient has or is at risk of developing AHR, a suitable single dose of an agent comprises a dose that improves AHR by a doubling dose of a provoking agent or improves the static respiratory function of an animal.

According to the method of the present invention, an effective amount of an agent that inhibits AHR to administer to an animal comprises an amount that is capable of reducing airway hyperresponsiveness (AHR) or airway inflammation without being toxic to the animal. An amount that is toxic to an animal comprises any amount that causes damage to the structure or function of an animal (i.e., poisonous).

In one embodiment of the present invention, in an animal that has AHR, an effective amount of an agent to administer to an animal is an amount that measurably reduces AHR in the animal as compared to prior to administration of the agent. In another embodiment, an effective amount of an agent to administer to an animal is an amount that measurably reduces AHR in the animal as compared to a level of airway AHR in a population of animals with inflammation that is associated with AHR wherein the agent was not administered. The agent is preferably capable of reducing AHR in an animal, even when the agent is administered after the onset of the physical symptoms of AHR (i.e., after acute onset AHR). Most preferably, an effective amount of the agent is an amount that reduces the symptoms of AHR to the point where AHR is no longer detected in the patient. In another embodiment, an effective amount of the agent is an amount that prevents, or substantially inhibits the onset of AHR when the agent is administered prior to exposure of the patient to an AHR-provoking stimulus, such as an allergen, in a manner sufficient to induce AHR in the absence of the agent.

One of skill in the art will be able to determine that the number of doses of an agent to be administered to an animal is dependent upon the extent of the airway hyperresponsiveness and the underlying condition of which AHR is a symptom, and the response of an individual patient to the treatment. In addition, the clinician will be able to determine the appropriate timing for delivery of the agent in a manner effective to reduce AHR in the animal. Preferably, the agent is delivered within 48 hours prior to exposure of the patient to an amount of an AHR provoking stimulus effective to induce AHR, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of AHR provoking stimulus effective to induce AHR. In one embodiment, the agent is administered as soon as it is recognized (i.e., immediately) by the patient or clinician that the patient has been exposed or is about to be exposed to an AHR provoking stimulus, and especially an AHR provoking stimulus to which the patient is sensitized (i.e., an allergen). In another embodiment, the agent is administered upon the first sign of development of AHR (i.e., acute onset AHR), and preferably, within at least 2 hours of the development of symptoms of AHR, and more preferably, within at least 1 hour, and more preferably within at least 30 minutes, and more preferably within at least 10 minutes, and more preferably within at least 5 minutes of development of symptoms of AHR. Symptoms of AHR and methods for measuring or detecting such symptoms have been described in detail above. Preferably, such administrations are given until signs of reduction of AHR appear, and then as needed until the symptoms of AHR are gone.

With particular regard to the method of inhibiting or preventing ischemia-reperfusion injury, an effective amount of an agent, and particularly an anti-factor B antibody or antigen binding fragment thereof (or antigen binding polypeptide) to administer to an animal is an amount that measurably inhibits histological damage, including oxidative damage or cell death, in the animal as compared to in the absence of administration of the agent. In the case of renal ischemia-reperfusion injury, an effective amount of an agent to administer to an animal is an amount that measurably inhibits increases in serum urea nitrogen or measurably decreases histologic injury to the tissues of the kidney of the animal as compared to in the absence of administration of the agent. A suitable single dose of an inhibitory agent to administer to an animal is a dose that is capable of reducing or preventing at least one symptom, type of injury, or resulting damage, from ischemia-reperfusion injury in an animal when administered one or more times over a suitable time period. Suitable doses of antibodies, including for various routes of administration, are described in detail above. In one aspect, an effective amount of an agent that inhibits ischemia-reperfusion injury to administer to an animal comprises an amount that is capable of inhibiting at least one symptom or damage caused by ischemia-reperfusion injury without being toxic to the animal.

Any of the methods of the present invention can be used in any animal, and particularly, in any animal of the vertebrate class Mammalia (i.e., mammals), including, without limitation, primates, rodents, livestock and domestic pets. Preferred mammals to treat with the methods of the present invention are humans.

---

We claim:

1. A method of reducing airway hyperresponsiveness (AHR) or airway inflammation comprising administering a composition comprising an engineered human anti-factor B antibody or antigen-binding fragment thereof and a pharmaceutically acceptable carrier to an individual in need thereof, wherein the engineered human anti-factor B antibody or antigen-binding fragment thereof comprises:
   a) a $V_K$-region comprising the amino acid sequence of SEQ ID NO:16 and a $V_H$-region comprising the amino acid sequence of SEQ ID NO:17;
   b) a $V_K$-region comprising the amino acid sequence of SEQ ID NO:18 and a $V_H$-region comprising the amino acid sequence of SEQ ID NO:19;
   c) a $V_K$-region comprising the amino acid sequence of SEQ ID NO:20 and a $V_H$-region comprising the amino acid sequence of SEQ ID NO:21;
   d) a $V_K$-region comprising the amino acid sequence of SEQ ID NO:16 and a $V_H$-region comprising the amino acid sequence of SEQ ID NO:35;
   e) a $V_K$-region comprising the amino acid sequence of SEQ ID NO:18 and a $V_H$-region comprising the amino acid sequence of SEQ ID NO:36; or
   f) a $V_K$-region comprising the amino acid sequence of SEQ ID NO:20 and a $V_H$-region comprising the amino acid sequence of SEQ ID NO:37,
   wherein the antigen-binding fragment is selected from the group consisting of Fab', (Fab')$_2$ Fv, scFv, and diabodies and wherein the engineered human anti-factor B antibody or antigen-binding fragment thereof reduces C3bBb complex formation in the individual.

2. The method of claim 1, wherein the engineered human anti-factor B antibody or antigen-binding fragment thereof is administered to the individual in an amount effective to measurably reduce AHR or airway inflammation in the animal as compared to before administration of the antibody or antigen-binding fragment thereof.

3. The method of claim 2, wherein said AHR or airway inflammation is associated with a disease selected from the group consisting of asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

4. The method of claim 2, wherein the AHR or airway inflammation is associated with allergic inflammation.

5. The method of claim 2, wherein the AHR or airway inflammation is associated with asthma.

6. The method of claim 2, wherein the AHR or airway inflammation is associated with COPD.

7. A method comprising administering a composition comprising an engineered human anti-factor B antibody or antigen-binding fragment thereof and a pharmaceutically acceptable carrier to an individual in need thereof, wherein the engineered human anti-factor B antibody or antigen-binding fragment thereof comprises:
   a) a $V_K$-region comprising the amino acid sequence of SEQ ID NO:16 and a $V_H$-region comprising the amino acid sequence of SEQ ID NO:17;
   b) a $V_K$-region comprising the amino acid sequence of SEQ ID NO:18 and a $V_H$-region comprising the amino acid sequence of SEQ ID NO:19;
   c) a $V_K$-region comprising the amino acid sequence of SEQ ID NO:20 and a $V_H$-region comprising the amino acid sequence of SEQ ID NO:21;
   d) a $V_K$-region comprising the amino acid sequence of SEQ ID NO:16 and a $V_H$-region comprising the amino acid sequence of SEQ ID NO:35;
   e) a $V_K$-region comprising the amino acid sequence of SEQ ID NO:18 and a $V_H$-region comprising the amino acid sequence of SEQ ID NO:36; or
   f) $V_K$-region comprising the amino acid sequence of SEQ ID NO:20 and a $V_H$-region comprising the amino acid sequence of SEQ ID NO:37, wherein the antigen-binding fragment is selected from the group consisting of Fab', (Fab')$_2$ Fv, scFv, and diabodies and wherein the engineered human anti-factor B antibody or antigen-binding fragment thereof reduces C3bBb complex formation in the individual.

8. The method of claim 7, wherein the antigen-binding fragment is a Fab'.

9. The method of claim 7, wherein the antigen-binding fragment is a Fab'.

10. The method of claim 1, wherein the engineered human antibody or antigen-binding fragment thereof has an equilibrium dissociation constant ("$K_D$") between about $1.0\times10^{-8}$ M and about $1.0\times10^{-10}$ M.

11. The method of claim 10, wherein the engineered human antibody or antigen-binding fragment thereof has an equilibrium dissociation constant ("$K_D$") between about $3.0\times10^{-9}$ M and about $7.0\times10^{-9}$ M.

12. The method of claim 1 wherein the engineered human anti-factor B antibody or antigen-binding fragment thereof further comprises a targeting ligand.

13. The method of claim 1, further comprising administering an anti-inflammatory agent.

14. The method of claim 1, wherein the individual is a human.

15. The method of claim 7, wherein the engineered human antibody or antigen-binding fragment thereof has an equilibrium dissociation constant ("$K_D$") between about $1.0\times10^{-8}$ M and about $1.010^{-1}$M.

16. The method of claim 15, wherein the engineered human antibody or antigen-binding fragment thereof has an equilibrium dissociation constant ("$K_D$") between about $3.0\times10^{-9}$ M and about $7.0\times10^{-9}$ M.

17. The method of claim 7, wherein the engineered human anti-factor B antibody or antigen-binding fragment thereof further comprises a targeting ligand.

18. The method of claim 7, further comprising administering an anti-inflammatory agent.

19. The method of claim 7, wherein the individual is a human.

20. The method of claim 7, wherein the antigen-binding fragment is a Fab'.

21. The method of claim 7, wherein the composition is formulated for administration by a route selected from the group consisting of oral, nasal, topical, inhalation, intratracheal, transdermal, rectal, and parenteral.

22. The method of claim 1, wherein the composition is formulated for administration by a route selected from the group consisting of oral, nasal, topical, inhalation, intratracheal, transdermal, rectal, and parenteral.

* * * * *

SEQUENCE LISTING

```
<160> NUMBER OF SEQ ID NOS: 37

<210> SEQ ID NO 1
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: V-Kappa-4 forward primer

<400> SEQUENCE: 1
tcagcttcyt gctaatcagt g                                            21

<210> SEQ ID NO 2
<211> LENGTH: 32
<212> TYPE: DNA
<213> ORGANISM: Mus musculus
<220> FEATURE:
<221> NAME/KEY: misc_feature
<222> LOCATION: (1)..(32)
<223> OTHER INFORMATION: V-Kappa-4 reverse primer

<400> SEQUENCE: 2
cgactagtcg actggtggga agatggatac ag                                32

<210> SEQ ID NO 3
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: V-Kappa-10 forward primer

<400> SEQUENCE: 3
tgttttcaag gtrccagatg t                                            21

<210> SEQ ID NO 4
<211> LENGTH: 32
```

```
<212> TYPE: DNA
<213> ORGANISM: Mus musculus
<220> FEATURE:
<221> NAME/KEY: misc_feature
<222> LOCATION: (1)..(32)
<223> OTHER INFORMATION: V-Kappa-10 reverse primer

<400> SEQUENCE: 4
cgactagtcg actggtggga agatggatac ag                                    32

<210> SEQ ID NO 5
<211> LENGTH: 20
<212> TYPE: DNA
<213> ORGANISM: Mus musculus
<220> FEATURE:
<221> NAME/KEY: misc_feature
<222> LOCATION: (1)..(32)
<223> OTHER INFORMATION: V-Heavy-6 forward primer

<400> SEQUENCE: 5
ctyttaaaag gkgtccagwg                                                  20

<210> SEQ ID NO 6
<211> LENGTH: 32
<212> TYPE: DNA
<213> ORGANISM: Mus musculus
<220> FEATURE:
<221> NAME/KEY: misc_feature
<222> LOCATION: (1)..(32)
<223> OTHER INFORMATION: V-Heavy-6 reverse primer

<400> SEQUENCE: 6
cgacaagtcg actagccctt gaccaggcat cc                                    32

<210> SEQ ID NO 7
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: V-Heavy-7 forward primer

<400> SEQUENCE: 7
cytttamatg gtatccagtg t                                                21

<210> SEQ ID NO 8
<211> LENGTH: 32
<212> TYPE: DNA
<213> ORGANISM: Mus musculus
<220> FEATURE:
<221> NAME/KEY: misc_feature
<222> LOCATION: (1)..(32)
<223> OTHER INFORMATION: V-Heavy-7 reverse primer

<400> SEQUENCE: 8
cgacaagtcg actagccctt gaccaggcat cc                                    32

<210> SEQ ID NO 9
<211> LENGTH: 114
<212> TYPE: PRT
<213> ORGANISM: Mus musculus
<220> FEATURE:
<221> NAME/KEY: VARIANT
<222> LOCATION: (1)..(114)
<223> OTHER INFORMATION: V-Kappa-4 PCR

<400> SEQUENCE: 9
```

-continued

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro Trp Thr Phe Gly Gly Gly Thr Lys Leu Glu Ile
            100                 105                 110

Lys Arg
```

<210> SEQ ID NO 10
<211> LENGTH: 120
<212> TYPE: PRT
<213> ORGANISM: Mus musculus
<220> FEATURE:
<221> NAME/KEY: VARIANT
<222> LOCATION: (1)..(120)
<223> OTHER INFORMATION: V-Heavy-6 PCR

<400> SEQUENCE: 10

```
Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Tyr Tyr Ser Asn Ser Ala Trp Phe Ala Tyr Trp Gly Gln
            100                 105                 110

Gly Thr Leu Val Thr Val Ser Ala
        115                 120
```

<210> SEQ ID NO 11
<211> LENGTH: 120
<212> TYPE: PRT
<213> ORGANISM: Mus musculus
<220> FEATURE:
<221> NAME/KEY: VARIANT
<222> LOCATION: (1)..(120)
<223> OTHER INFORMATION: V-Heavy-7 PCR

<400> SEQUENCE: 11

```
Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45
```

```
Gly Asp Ile Asn Pro Asn Asn Gly Gly Thr Ile Tyr Asn Gln Lys Phe
        50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Thr Ala Val Tyr Tyr Cys
                85                  90                  95

Ala Arg Gly Tyr Tyr Ser Asn Ser Ala Trp Phe Ala Tyr Trp Gly Gln
                100                 105                 110

Gly Thr Leu Val Thr Val Ser Ala
            115                 120

<210> SEQ ID NO 12
<211> LENGTH: 113
<212> TYPE: PRT
<213> ORGANISM: Homo sapien
<220> FEATURE:
<221> NAME/KEY: VARIANT
<222> LOCATION: (1)..(113)
<223> OTHER INFORMATION: germline V-Kappa-IV-B3/J-Kappa-2

<400> SEQUENCE: 12

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Leu Glu Ile
                100                 105                 110

Lys

<210> SEQ ID NO 13
<211> LENGTH: 113
<212> TYPE: PRT
<213> ORGANISM: Homo sapien
<220> FEATURE:
<221> NAME/KEY: VARIANT
<222> LOCATION: (1)..(113)
<223> OTHER INFORMATION: germline V-Heavy-1-02/J-Heavy-4

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
```

Ala Arg Tyr Phe Asp Tyr Trp Gly Gln Gly Thr Leu Val Thr Val Ser
            100                 105                 110
Ser

<210> SEQ ID NO 14
<211> LENGTH: 113
<212> TYPE: PRT
<213> ORGANISM: Mus musculus
<220> FEATURE:
<221> NAME/KEY: VARIANT
<222> LOCATION: (1)..(113)
<223> OTHER INFORMATION: V-Kappa domain from TA10 reference Ab

<400> SEQUENCE: 14

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro Trp Thr Phe Gly Gln Gly Thr Lys Leu Glu Ile
            100                 105                 110

Lys

<210> SEQ ID NO 15
<211> LENGTH: 120
<212> TYPE: PRT
<213> ORGANISM: Mus musculus
<220> FEATURE:
<221> NAME/KEY: VARIANT
<222> LOCATION: (1)..(120)
<223> OTHER INFORMATION: V-Heavy domain from TA10 reference Ab

<400> SEQUENCE: 15

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Tyr Tyr Ser Asn Ser Ala Trp Phe Ala Tyr Trp Gly Gln
            100                 105                 110

Gly Thr Leu Val Thr Val Ser Ser
        115                 120

-continued

```
<210> SEQ ID NO 16
<211> LENGTH: 113
<212> TYPE: PRT
<213> ORGANISM: Artificial Sequence
<220> FEATURE:
<223> OTHER INFORMATION: V-Kappa domain from TA101-1

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Asn Ser
            20                  25                  30

Ser Thr Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys

<210> SEQ ID NO 17
<211> LENGTH: 120
<212> TYPE: PRT
<213> ORGANISM: Artificial Sequence
<220> FEATURE:
<223> OTHER INFORMATION: V-Heavy domain from TA101-1

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 18
<211> LENGTH: 113
<212> TYPE: PRT
<213> ORGANISM: Artificial Sequence
<220> FEATURE:
<223> OTHER INFORMATION: V-Kappa domain from TA102-4

<400> SEQUENCE: 18

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Val Leu Asn Ser
            20                  25                  30

Arg Asn Lys Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys

<210> SEQ ID NO 19
<211> LENGTH: 120
<212> TYPE: PRT
<213> ORGANISM: Artificial Sequence
<220> FEATURE:
<223> OTHER INFORMATION: V-Heavy domain from TA102-4

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 20
<211> LENGTH: 113
<212> TYPE: PRT
<213> ORGANISM: Artificial Sequence
<220> FEATURE:
<223> OTHER INFORMATION: V-Kappa domain from TA103-2

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

-continued

```
Ile Ser Ser Leu Gln Ala Glu Asp Val Ala Val Tyr Tyr Cys Lys Gln
            85                  90                  95

Val Tyr Asn Leu Pro Trp Thr Phe Gly Gln Gly Thr Lys Leu Glu Ile
        100                 105                 110

Lys

<210> SEQ ID NO 21
<211> LENGTH: 120
<212> TYPE: PRT
<213> ORGANISM: Artificial Sequence
<220> FEATURE:
<223> OTHER INFORMATION: V-Heavy domain from TA103-2

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 22
<211> LENGTH: 19
<212> TYPE: PRT
<213> ORGANISM: Mus musculus
<220> FEATURE:
<221> NAME/KEY: VARIANT
<222> LOCATION: (1)..(19)
<223> OTHER INFORMATION: V-Kappa CDR3-FR4 domain of TA10 reference Ab

<400> SEQUENCE: 22

Lys Gln Ser Tyr Asn Leu Pro Trp Thr Phe Gly Gln Gly Thr Lys Leu
1               5                   10                  15

Glu Ile Lys

<210> SEQ ID NO 23
<211> LENGTH: 22
<212> TYPE: PRT
<213> ORGANISM: Mus musculus
<220> FEATURE:
<221> NAME/KEY: VARIANT
<222> LOCATION: (1)..(22)
<223> OTHER INFORMATION: V-Heavy CDR3-FR4 domain of TA10 reference Ab

<400> SEQUENCE: 23

Gly Tyr Tyr Ser Asn Ser Ala Trp Phe Ala Tyr Trp Gly Gln Gly Thr
1               5                   10                  15

Leu Val Thr Val Ser Ser
            20

<210> SEQ ID NO 24
```

```
<211> LENGTH: 19
<212> TYPE: PRT
<213> ORGANISM: Artificial Sequence
<220> FEATURE:
<223> OTHER INFORMATION: V-Kappa CDR3-FR4 domain of TA101-1

<400> SEQUENCE: 24

Lys Gln Val Tyr Asn Leu Pro Trp Thr Phe Gly Gln Gly Thr Lys Leu
1               5                   10                  15

Glu Ile Lys

<210> SEQ ID NO 25
<211> LENGTH: 22
<212> TYPE: PRT
<213> ORGANISM: Artificial Sequence
<220> FEATURE:
<223> OTHER INFORMATION: V-Kappa CDR3-FR4 domain of TA101-1

<400> SEQUENCE: 25

Gly Tyr Tyr Ala Asn Ser Ala Trp Phe Ala Tyr Trp Gly Gln Gly Thr
1               5                   10                  15

Leu Val Thr Val Ser Ser
            20

<210> SEQ ID NO 26
<211> LENGTH: 19
<212> TYPE: PRT
<213> ORGANISM: Artificial Sequence
<220> FEATURE:
<223> OTHER INFORMATION: V-Kappa CDR3-FR4 domain of TA102-4

<400> SEQUENCE: 26

Lys Gln Val Tyr Asn Leu Pro Trp Thr Phe Gly Gln Gly Thr Lys Leu
1               5                   10                  15

Glu Ile Lys

<210> SEQ ID NO 27
<211> LENGTH: 22
<212> TYPE: PRT
<213> ORGANISM: Artificial Sequence
<220> FEATURE:
<223> OTHER INFORMATION: V-Heavy CDR3-FR4 domain of TA102-4

<400> SEQUENCE: 27

Gly Tyr Tyr Ala Asn Ser Ala Trp Phe Ala Tyr Trp Gly Gln Gly Thr
1               5                   10                  15

Leu Val Thr Val Ser Ser
            20

<210> SEQ ID NO 28
<211> LENGTH: 19
<212> TYPE: PRT
<213> ORGANISM: Artificial Sequence
<220> FEATURE:
<223> OTHER INFORMATION: V-Kappa CDR3-FR4 domain of TA103-2

<400> SEQUENCE: 28

Lys Gln Val Tyr Asn Leu Pro Trp Thr Phe Gly Gln Gly Thr Lys Leu
1               5                   10                  15

Glu Ile Lys

<210> SEQ ID NO 29
<211> LENGTH: 22
<212> TYPE: PRT
```

<213> ORGANISM: Artificial Sequence
<220> FEATURE:
<223> OTHER INFORMATION: V-Heavy CDR3-FR4 domain of TA103-2

<400> SEQUENCE: 29

Gly Tyr Tyr Ala Asn Ser Ala Trp Phe Ala Tyr Trp Gly Gln Gly Thr
1               5                   10                  15

Leu Val Thr Val Ser Ser
            20

<210> SEQ ID NO 30
<211> LENGTH: 739
<212> TYPE: PRT
<213> ORGANISM: Homo sapien
<220> FEATURE:
<221> NAME/KEY: VARIANT
<222> LOCATION: (1)..(739)
<223> OTHER INFORMATION: secreted factor B

<400> SEQUENCE: 30

Thr Pro Trp Ser Leu Ala Arg Pro Gln Gly Ser Cys Ser Leu Glu Gly
1               5                   10                  15

Val Glu Ile Lys Gly Gly Ser Phe Arg Leu Leu Gln Glu Gly Gln Ala
            20                  25                  30

Leu Glu Tyr Val Cys Pro Ser Gly Phe Tyr Pro Tyr Pro Val Gln Thr
        35                  40                  45

Arg Thr Cys Arg Ser Thr Gly Ser Trp Ser Thr Leu Lys Thr Gln Asp
    50                  55                  60

Gln Lys Thr Val Arg Lys Ala Glu Cys Arg Ala Ile His Cys Pro Arg
65                  70                  75                  80

Pro His Asp Phe Glu Asn Gly Glu Tyr Trp Pro Arg Ser Pro Tyr Tyr
                85                  90                  95

Asn Val Ser Asp Glu Ile Ser Phe His Cys Tyr Asp Gly Tyr Thr Leu
            100                 105                 110

Arg Gly Ser Ala Asn Arg Thr Cys Gln Val Asn Gly Arg Trp Ser Gly
        115                 120                 125

Gln Thr Ala Ile Cys Asp Asn Gly Ala Gly Tyr Cys Ser Asn Pro Gly
    130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys Lys Cys Leu Val Asn Leu Ile
            260                 265                 270

Glu Lys Val Ala Ser Tyr Gly Val Lys Pro Arg Tyr Gly Leu Val Thr
        275                 280                 285

Tyr Ala Thr Tyr Pro Lys Ile Trp Val Lys Val Ser Glu Ala Asp Ser

```
                290                 295                 300
Ser Asn Ala Asp Trp Val Thr Lys Gln Leu Asn Glu Ile Asn Tyr Glu
305                 310                 315                 320

Asp His Lys Leu Lys Ser Gly Thr Asn Thr Lys Lys Ala Leu Gln Ala
                325                 330                 335

Val Tyr Ser Met Met Ser Trp Pro Asp Asp Val Pro Pro Glu Gly Trp
            340                 345                 350

Asn Arg Thr Arg His Val Ile Ile Leu Met Thr Asp Gly Leu His Asn
            355                 360                 365

Met Gly Gly Asp Pro Ile Thr Val Ile Asp Glu Ile Arg Asp Leu Leu
        370                 375                 380

Tyr Ile Gly Lys Asp Arg Lys Asn Pro Arg Glu Asp Tyr Leu Asp Val
385                 390                 395                 400

Tyr Val Phe Gly Val Gly Pro Leu Val Asn Gln Val Asn Ile Asn Ala
                405                 410                 415

Leu Ala Ser Lys Lys Asp Asn Glu Gln His Val Phe Lys Val Lys Asp
                420                 425                 430

Met Glu Asn Leu Glu Asp Val Phe Tyr Gln Met Ile Asp Glu Ser Gln
            435                 440                 445

Ser Leu Ser Leu Cys Gly Met Val Trp Glu His Arg Lys Gly Thr Asp
        450                 455                 460

Tyr His Lys Gln Pro Trp Gln Ala Lys Ile Ser Val Ile Arg Pro Ser
465                 470                 475                 480

Lys Gly His Glu Ser Cys Met Gly Ala Val Val Ser Glu Tyr Phe Val
                485                 490                 495

Leu Thr Ala Ala His Cys Phe Thr Val Asp Asp Lys Glu His Ser Ile
                500                 505                 510

Lys Val Ser Val Gly Gly Glu Lys Arg Asp Leu Glu Ile Glu Val Val
            515                 520                 525

Leu Phe His Pro Asn Tyr Asn Ile Asn Gly Lys Lys Glu Ala Gly Ile
        530                 535                 540

Pro Glu Phe Tyr Asp Tyr Asp Val Ala Leu Ile Lys Leu Lys Asn Lys
545                 550                 555                 560

Leu Lys Tyr Gly Gln Thr Ile Arg Pro Ile Cys Leu Pro Cys Thr Glu
                565                 570                 575

Gly Thr Thr Arg Ala Leu Arg Leu Pro Pro Thr Thr Thr Cys Gln Gln
            580                 585                 590

Gln Lys Glu Glu Leu Leu Pro Ala Gln Asp Ile Lys Ala Leu Phe Val
        595                 600                 605

Ser Glu Glu Glu Lys Lys Leu Thr Arg Lys Glu Val Tyr Ile Lys Asn
610                 615                 620

Gly Asp Lys Lys Gly Ser Cys Glu Arg Asp Ala Gln Tyr Ala Pro Gly
625                 630                 635                 640

Tyr Asp Lys Val Lys Asp Ile Ser Glu Val Val Thr Pro Arg Phe Leu
                645                 650                 655

Cys Thr Gly Gly Val Ser Pro Tyr Ala Asp Pro Asn Thr Cys Arg Gly
            660                 665                 670

Asp Ser Gly Gly Pro Leu Ile Val His Lys Arg Ser Arg Phe Ile Gln
        675                 680                 685

Val Gly Val Ile Ser Trp Gly Val Val Asp Val Cys Lys Asn Gln Lys
        690                 695                 700

Arg Gln Lys Gln Val Pro Ala His Ala Arg Asp Phe His Ile Asn Leu
705                 710                 715                 720
```

Phe Gln Val Leu Pro Trp Leu Lys Glu Lys Leu Gln Asp Glu Asp Leu
                725                 730                 735

Gly Phe Leu

<210> SEQ ID NO 31
<211> LENGTH: 19
<212> TYPE: PRT
<213> ORGANISM: Mus musculus
<220> FEATURE:
<221> NAME/KEY: VARIANT
<222> LOCATION: (1)..(19)
<223> OTHER INFORMATION: Amino-terminal sequence of V-Heavy chain of
      mAb 1379 (1379H)

<400> SEQUENCE: 31

Glu Val Gln Gln Ser Gly Pro Glu Leu Val Lys Pro Gly Ala Ser Val
1               5                   10                  15

Lys Ile Pro

<210> SEQ ID NO 32
<211> LENGTH: 25
<212> TYPE: PRT
<213> ORGANISM: Mus musculus
<220> FEATURE:
<221> NAME/KEY: VARIANT
<222> LOCATION: (1)..(25)
<223> OTHER INFORMATION: Amino-terminal sequence of V-Kappa chain of
      mAb 1379 (1379L)

<400> SEQUENCE: 32

Asp Ile Val Met Ser Gln Ser Pro Ser Ser Leu Ala Val Ser Ala Gly
1               5                   10                  15

Glu Lys Val Thr Met Ser Ser Lys Lys
            20                  25

<210> SEQ ID NO 33
<211> LENGTH: 21
<212> TYPE: PRT
<213> ORGANISM: Mus musculus
<220> FEATURE:
<221> NAME/KEY: VARIANT
<222> LOCATION: (1)..(21)
<223> OTHER INFORMATION: Amino-terminal sequence of V-Heavy-6
      (TA-V-Heavy-6) clone

<400> SEQUENCE: 33

Glu Val Gln Leu Gln Gln Ser Gly Pro Glu Leu Val Lys Pro Gly Ala
1               5                   10                  15

Ser Val Lys Ile Pro
            20

<210> SEQ ID NO 34
<211> LENGTH: 25
<212> TYPE: PRT
<213> ORGANISM: Mus musculus
<220> FEATURE:
<221> NAME/KEY: VARIANT
<222> LOCATION: (1)..(25)
<223> OTHER INFORMATION: Amino-terminal sequence of V-Kappa-4
      (TA-V-Kappa-4) clone

<400> SEQUENCE: 34

Asp Ile Val Met Ser Gln Ser Pro Ser Ser Leu Ala Val Ser Ala Gly
1               5                   10                  15

Glu Lys Val Thr Met Ser Cys Lys Ser 20          25

<210> SEQ ID NO 35
<211> LENGTH: 120
<212> TYPE: PRT
<213> ORGANISM: Artificial Sequence
<220> FEATURE:
<223> OTHER INFORMATION: V-Heavy domain from TA101-1 with Q to E
      substitution

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: V-Heavy domain from TA102-4 with Q to E
      substitution

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 37
<211> LENGTH: 120
<212> TYPE: PRT
<213> ORGANISM: Artificial Sequence
<220> FEATURE:
<223> OTHER INFORMATION: V-Heavy domain from TA103-2 with Q to E -continued

```
      substitution

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
            115             120
```